United States Patent
Pasquet et al.

(10) Patent No.: US 12,268,700 B2
(45) Date of Patent: Apr. 8, 2025

(54) 3-O-SULFO-GALACTOSYLCERAMIDE ANALOGS AS ACTIVATORS OF TYPE II NKT CELLS AND USES THEREOF

(71) Applicants: The United States of America, as represented by the Secretary, Department of Health and Human Services, Bethesda, MD (US); University of Connecticut, Farmington, CT (US)

(72) Inventors: Lise H. Pasquet, Saint-Pierre-du-Mont (FR); Jay A. Berzofsky, Bethesda, MD (US); Amy R. Howell, Storrs, CT (US); Masaki Terabe, Potomac, MD (US); Kaddy Camara, Storrs, CT (US); Stewart K. Richardson, Storrs, CT (US)

(73) Assignees: The United States of America, as represented by the Secretary, Department of Health and Human Services, Bethesda, MD (US); University of Connecticut, Farmington, CT (US)

( * ) Notice: Subject to any disclaimer, the term of this patent is extended or adjusted under 35 U.S.C. 154(b) by 1011 days.

(21) Appl. No.: 17/041,604

(22) PCT Filed: Mar. 25, 2019

(86) PCT No.: PCT/US2019/023890
§ 371 (c)(1),
(2) Date: Sep. 25, 2020

(87) PCT Pub. No.: WO2019/190986
PCT Pub. Date: Oct. 3, 2019

(65) Prior Publication Data
US 2021/0023110 A1    Jan. 28, 2021

Related U.S. Application Data

(60) Provisional application No. 62/648,167, filed on Mar. 26, 2018.

(51) Int. Cl.
*A61K 31/7032* (2006.01)
*A61K 38/17* (2006.01)
*A61K 38/19* (2006.01)
*A61K 39/395* (2006.01)
*A61P 35/00* (2006.01)
*C07H 15/04* (2006.01)
*C07H 15/10* (2006.01)

(52) U.S. Cl.
CPC ...... *A61K 31/7032* (2013.01); *A61K 38/1774* (2013.01); *A61K 38/193* (2013.01); *A61K 39/3955* (2013.01); *A61P 35/00* (2018.01); *C07H 15/04* (2013.01); *C07H 15/10* (2013.01)

(58) Field of Classification Search
CPC ................................................. A61K 31/7032
See application file for complete search history.

(56) References Cited

U.S. PATENT DOCUMENTS 8,227,581 B2 *   7/2012   Savage ................. C07H 15/06
                                                          536/1.11

FOREIGN PATENT DOCUMENTS

| WO | WO 2008/005824 A1 | 1/2008 | |
| WO | WO 2008005824 | * 10/2008 | ............. A01N 37/00 |
| WO | WO 2016/094226 A1 | 6/2016 | |
| WO | WO 2016094226 | * 6/2016 | ............. A01N 37/00 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home > Thesis Resources > Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*

(Continued)

*Primary Examiner* — Nizal S Chandrakumar
(74) *Attorney, Agent, or Firm* — Leydig, Voit & Mayer, Ltd.

(57) ABSTRACT

Disclosed is a compound of the formula (I) or (II): wherein a f are as described herein. The compounds are useful in the activation of Type II NKT cells and in treating cancer.

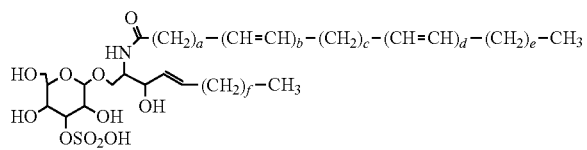

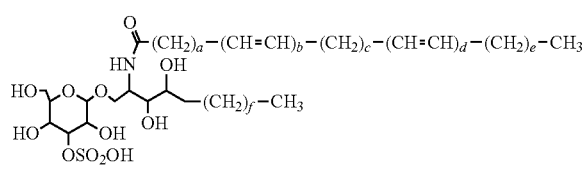

5 Claims, 9 Drawing Sheets

(56) References Cited

OTHER PUBLICATIONS

Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Nelson, The Current Landscape of NKT Cell Immunotherapy and the Hills Ahead. Cancers 2021, 13, 5174.*
Xing, Bioorganic & Medicinal Chemistry 13 (2005) 2907-2916.*
Pernber, Biochimica et Biophysica Acta 1771 (2007) 202-209.*
McConathy, Prim Care Companion J Clin Psychiatry. 2003; 5(2): 70-73.*
Sundaresan, Protein Science (2002), 11:1330-1339.*
Venkatesh, J. Pharm. Sci. 89, 145-154 (2000) (p. 146, left column).*
Cannon, Chapter Nineteen in Burger's Medicinal Chemistry and Drug Discovery, Fifth Edition, vol. I: Principles and Practice, Wiley-Interscience 1995, pp. 783-802, 784.*
Dorwald F. A. Side Reactions in Organic Synthesis, 2005, Wiley: VCH, Weinheim p. IX of Preface p. 1-15.*
Abrams et al., "Triple-Bond Isomerizations: 2- to 9-Decyn-1-OL," *Organic Syntheses, Coll.*, 8:146 (1993); 66:127 (1988).
Ambrosino et al., "Cross-Regulation between Type I and Type II NKT Cells in Regulating Tumor Immunity: A New Immunoregulatory Axis," *The Journal of Immunology*, 179:5126-5136 (2007).
Angel et al., "Enhanced Sensitivity for High Spatial Resolution Lipid Analysis by Negative Ion Mode MALDI Imaging Mass Spectrometry," *Anal. Chem.*, 84(3):1557-1564 (2012).
Bendelac et al., "A Subset of CD4+ Thymocytes Selected by MHC Class I Molecules," *Science*, 263(5154):1774-1778 (1994).
Bendelac et al., "CD1 Recognition by Mouse NK1+ T Lymphocytes," *Science*, 268(5212):863-865 (1995).
Blomqvist et al., "Multiple tissue-specific isoforms of sulfatide activate CD1d-restricted type II NKT cells," *European Journal of Immunology*, 39:1726-1735 (2009).
Brutkiewicz et al., "TAP-independent, $\beta_2$-Microglobulin-dependent Surface Expression of Functional Mouse CD1.1," *J. Exp. Med.*, 182:1913-1919 (1995).
Cardell et al., "CD1-restricted CD4+ T Cells in Major Histocompatibility Complex Class II-deficient Mice," *J. Exp. Med.*, 182:993-1004 (1995).
Chang et al., "Inflammation-associated lysophospholipids as ligands for CD1d-restricted T cells in human cancer," *Blood*, 112(4):1308-1316 (2008).
Compostella et al., "CD1a-binding glycosphingolipids stimulating human autoreactive T-cells: synthesis of a family of sulfatides differing in the acyl chain moiety," *Tetrahedron*, 58:8703-8708 (2002).
Compostella et al., "Chemoenzymatic steroconvergent synthesis of 3-O-benzoyl azidosphingosine," *Tetrahedron: Asymmetry*, 13:867-872 (2002).
European Patent Office, International Search Report in International Patent Application No. PCT/US2019/023890, mailed Aug. 9, 2019 (5 pp.).
European Patent Office, Written Opinion in International Patent Application No. PCT/US2019/023890, mailed Aug. 9, 2019 (7 pp.).
Girardi et al., "Type II Natural Killer T cells recognize sulfatide self-antigens using features of both innate-like and conventional T cells," *Nat. Immunol.*, 13(9):851-856 (2012).
Guilbert et al., "Dibutylstannylene Acetals: Userful Inermediates for the Regioselective Sulfation of Glycosides," *Tetrahedron: Asymmetry*, 5(11):2163-2178 (1994).
Gumperz et al., "Murine CD1d-Restricted T Cell Recognition of Cellular Lipids," *Immunity*, 12:211-221 (2000).
International Bureau of WIPO, International Preliminary Report on Patentability in International Patent Application No. PCT/US2019/023890, mailed Sep. 29, 2020 (9 pp.).
Izhak et al., "Delicate Balance among Three Types of T Cells in Concurrent Regulation of Tumor Immunity," *Cancer Res.*, 73(5):1514-1523 (2013).

Jahng et al., "Prevention of Autoimmunity by Targeting a Distinct, Noninvariant CD1d-reactive T Cell Population Reactive to Sulfatide," *J. Exp. Med.*, 199(7):947-957 (2004).
Kim et al., "Efficient Synthesis of D-erythro-Sphingosine and D-erythro-Azidosphingosine from D-ribo-Phytosphingosine via a Cyclic Sulfate Intermediate," *J. Org. Chem.*, 71:8661-8664 (2006).
Makowska et al., "Differences in the Ligand Specificity between CD1d-Restricted T Cells with Limited and Diverse T-Cell Receptor Repertoire," *Scand. J. Immunol.*, 52:71-79 (2000).
Maricic et al., "Recognition of Lysophosphatidylcholine by Type II NKT Cells and Protection from an Inflammatory Liver Disease," *The Journal of Immunology*, 193:4580-4589 (2014).
Mbadugha et al., "Sugar/Steroid/Sugar Conjugates: Sensitivity of Lipid Binding to Sugar Structure," *Organic Letters*, 5(22):4041-4044 (2003).
Nashed et al., "Selective Silylation of β-D-Galactosides. A New Approach to Synthesis of (1→6)-β-D-Galactopyranooligosaccharides," *J. Org. Chem.*, 52:5255-5260 (1987).
Pasquet et al., "The ceramide structure of sulfatide-analogues influences the functional activity of type II NKT cells," National Cancer Institute, CD1-MR1 Conference 2017, Poster, 1 page (Nov. 5, 2017).
Patel et al., "Recognition of CD1d-sulfatide mediated by a type II natural killer T cell antigen receptor," *Nature Immunology*, 13(9):857-863 (2012).
Pernber et al., "Sulfatide with different fatty acids has unique distributions in cerebellum as imaged by Time-Of-Flight Secondary Ion Mass Spectrometry (TOF-SIMS)," *Biochimica et Biophysica Acta*, 1771:202-209 (2007).
Rhost et al., "Identification of novel glycolipid ligands activating a sulfatide-reactive, CD1d-restricted, type II natural killer T lymphocyte," *European Journal of Immunology*, 42:2851-2860 (2012).
Subramanian et al., "NKT Cells Stimulated by Long Fatty Acyl Chain Sulfatides Significantly Reduces the Incidence of Type 1 Diabetes in Nonobese Diabetic Mice," *PloS One*, 7(5):e37771 (2012).
Tallman et al., "Substituent effects on regioselectivity in the autoxidation of nonconjugated dienes," *J. Am. Chem. Soc.*, 131(15):5635-5641 (2009).
Tatituri et al., "Recognition of microbial and mammalian phospholipid antigens by NKT cells with diverse TCRs," *PNAS*, 110(5):1827-1832 (2013).
Terabe et al., "Transforming Growth Factor-β Production and Myeloid Cells Are an Effector Mechanism through Which CD1d-restricted T Cells Block Cytotoxic T Lymphocyte-mediated Tumor Immunosurveillance: Abrogation Prevents Tumor Recurrence," *The Journal of Experimental Medicine*, 198(11):1741-1752 (2003).
Terabe et al., "NKT cell-mediated repression of tumor immunosurveillance by IL-13 and the IL-4R-STAT6 pathway," *Nature Immunology*, 1(6):515-520 (2000).
Trappeniers et al., "Synthesis and in vitro Evaluation of α-GalCer Epimers," *ChemMedChem*, 3:1061-1070 (2008).
Veerapen et al., "Synthesis and biological activity of α-galactosyl ceramide KRN7000 and galactosyl (α1→2) galactosyl ceramide," *Bioorganic & Medicinal Chemistry Letters*, 19:4288-4291 (2009).
Wolf et al., "Identification of a Potent Microbial Lipid Antigen for Diverse NKT Cells," *The Journal of Immunology*, 195:2540-2551 (2015).
Xing et al., "Synthesis and human NKT cell stimulating properties of 3-O-sulfo-α/β-galactosylceramides," *Bioorganic & Medicinal Chemistry*, 13:2907-2916 (2005).
Zhang et al., "Sulfatide-activated type II NKT cells prevent allergic airway inflammation by inhibiting type I NKT cell function in a mouse model of asthma," *Am. J. Physiol. Lung Cell Mol. Physiol.*, 301:L975-L984 (2011).
Zimmermann et al., "Azidosphingosine Glycosylation in Glycosphingolipid Synthesis," *Journal of Carbohydrate Chemistry*, 7(2):435-452 (1987) (Abstract).
Kronenberg et al., "NKT Cells in the Antitumor Response: the β Version?" The Journal of Clinical Investigation, 134(4): e177663 (2024) 3 pages.

(56) References Cited

OTHER PUBLICATIONS

Nishio et al., "Lysosomal Processing of Sulfatide Analogs Alters Target NKT Cell Specificity and Immune Responses in Cancer," The Journal of Clinical Investigation, 134(4): e165281 (2024) 15 pages.

* cited by examiner

3-O-SULFO-GALACTOSYLCERAMIDE ANALOGS AS ACTIVATORS OF TYPE II NKT CELLS AND USES THEREOF

CROSS-REFERENCE TO RELATED APPLICATIONS

This patent application is the national stage of International Patent Application No. PCT/US2019/023890, filed Mar. 25, 2019, which claims the benefit of U.S. Provisional Patent Application No. 62/648,167, filed Mar. 26, 2018, the disclosures of which are incorporated herein by reference in their entirety for all purposes.

STATEMENT REGARDING FEDERALLY SPONSORED RESEARCH OR DEVELOPMENT

This invention was made with Government support under Grant Numbers NCI Intramural Z01-C-004020 and 5U01GM111849 awarded by the National Institutes of Health, National Cancer Institute, and National Institute of General Medical Sciences (NIGMS). The Government has certain rights in this invention.

BACKGROUND OF THE INVENTION

Some cancers may have very limited treatment options. Despite advances in treatments such as, for example, surgery, chemotherapy, and radiation therapy, the prognosis for many cancers, such as, for example, lung cancer, colon cancer, liver cancer, melanoma, breast cancer, or uterine cervical cancer, may be poor. Accordingly, there exists an unmet need for additional treatments for cancer.

BRIEF SUMMARY OF THE INVENTION

An embodiment of the invention provides a compound of the formula (I) or (II):

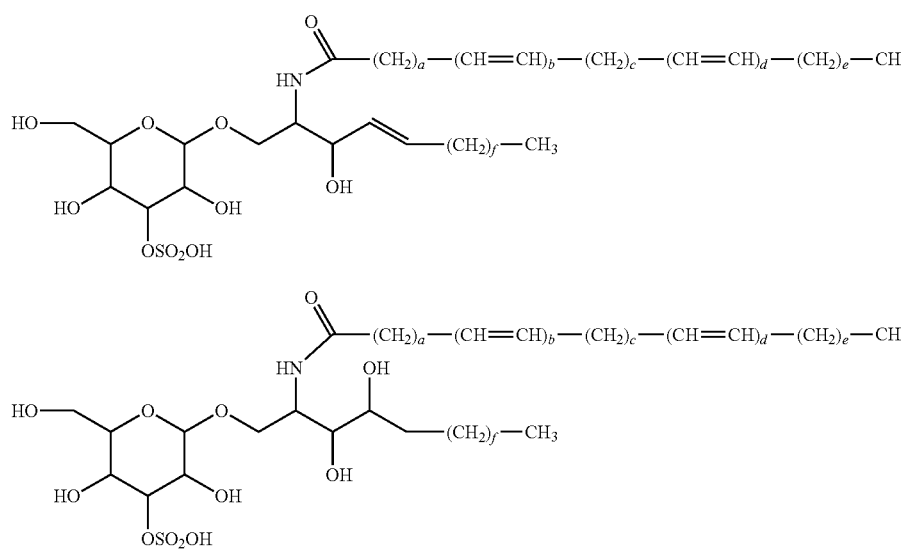

wherein a is an integer of from about 1 to about 20,
b is about 0 or about 1,
c is an integer of from about 1 to about 5,
d is about 0 or about 1,
e is an integer of from about 1 to about 10, and
f is an integer of from about 1 to about 20,
or a pharmaceutically acceptable salt thereof, solvate thereof, stereoisomer thereof, or mixture comprising stereoisomers thereof,
with the provisos that:
(i) when b is 1 and d is 0 in Formula (I), $a+c+e \neq 20$, and
(ii) when b and d are both 0 in Formula (II), $a+c+e \neq 22$ or 14.

Embodiments of the invention also provide a composition comprising a compound of an embodiment of the invention, salt thereof, solvate thereof, stereoisomer thereof, or mixture comprising stereoisomers and a pharmaceutically acceptable carrier.

An embodiment of the invention further provides a method of selectively activating type II NKT cells in vitro, the method comprising culturing in vitro a mononuclear cell fraction comprising one or more mammalian type II NKT cells in the presence of a composition comprising a compound of the invention, salt thereof, solvate thereof, stereoisomers thereof, or mixture comprising stereoisomers thereof in an amount sufficient to activate mammalian type II NKT cells in vitro.

An embodiment of the invention additionally provides a method of inducing an immune response, treating cancer, inhibiting growth of a tumor, or inhibiting metastasis of a tumor in a mammal in need thereof, comprising administering to the mammal a composition comprising a compound of the invention, salt thereof, solvate thereof, stereoisomer thereof, or mixture comprising stereoisomers thereof in an amount effective to induce an immune response, treat cancer, inhibit growth of a tumor, or inhibit metastasis of a tumor in the mammal.

An embodiment of the invention also provides a method of inhibiting a suppressive effect of type II NKT cells on an anti-cancer immune response in a mammal afflicted with the cancer, comprising administering to the mammal a composition comprising a compound of the invention, salt thereof, solvate thereof, stereoisomer thereof, or mixture comprising stereoisomers thereof in an amount effective to inhibit the suppressive effect of type II NKT cells on the anti-cancer immune response in the mammal.

An embodiment of the invention further provides a method of reducing a tumor burden in a mammal afflicted with a cancer, comprising administering to the mammal a composition comprising a compound of the invention, salt thereof, solvate thereof, stereoisomer thereof, or mixture comprising stereoisomers thereof in an amount effective to reduce the tumor burden in the mammal.

BRIEF DESCRIPTION OF THE SEVERAL VIEWS OF THE DRAWING(S)

Figure 4A:
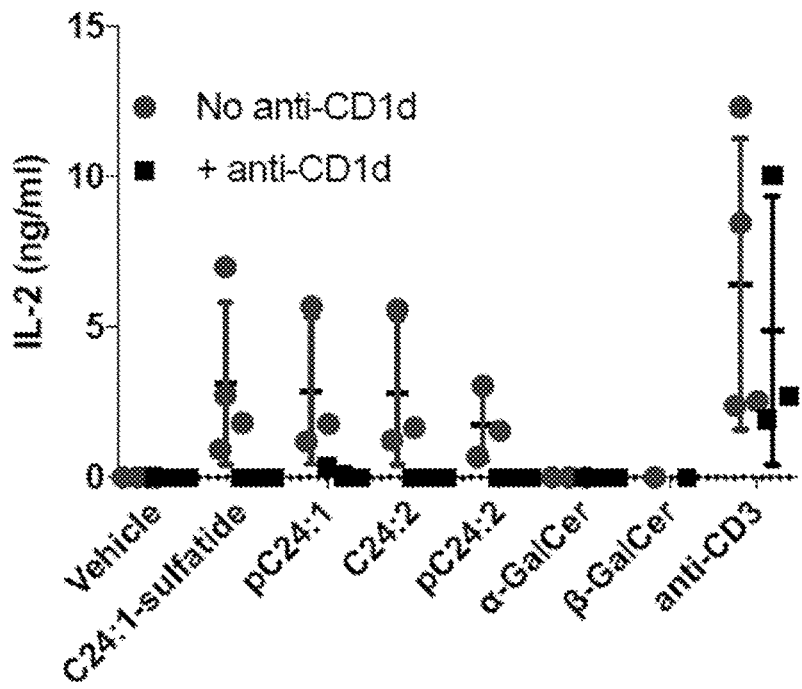
Figure 4B:
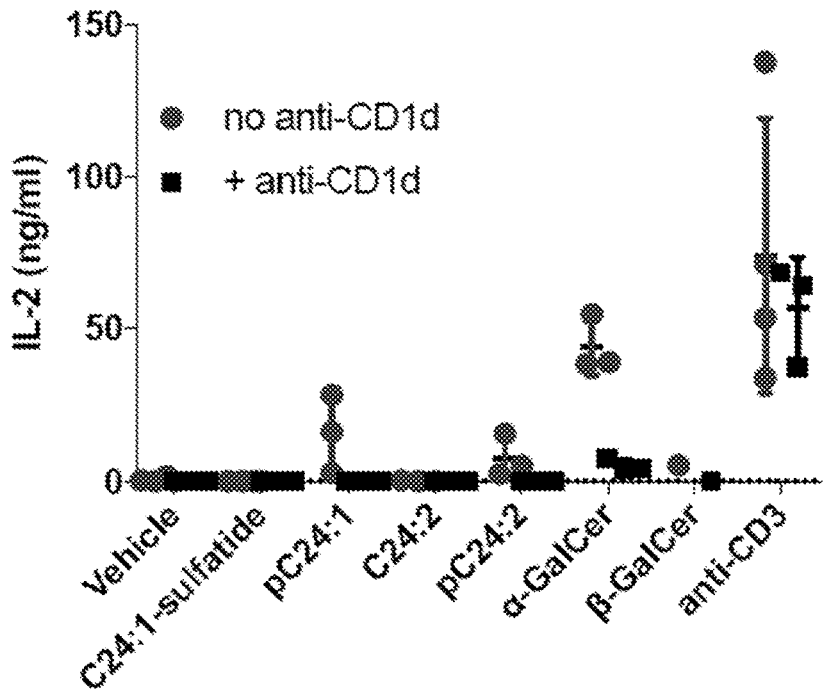

FIGS. 4A-4B show XV19 type II NKT hybridoma (FIG. 4A) and DN32 type I NKT hybridoma (FIG. 4B) stimulated 24 h with 0.5 μg of plate-coated CD1d monomers loaded with 4 μM of sulfatide or sulfatide analogues, 10 nM of α-GalCer or of β-GalCer or with 10 ng/ml of plate coated anti-CD3 antibody. The production of IL-2 was measured by ELISA (enzyme-linked immunosorbent assay) in the culture supernatant. n=4 points from 3 independent experiments.

Figure 5:
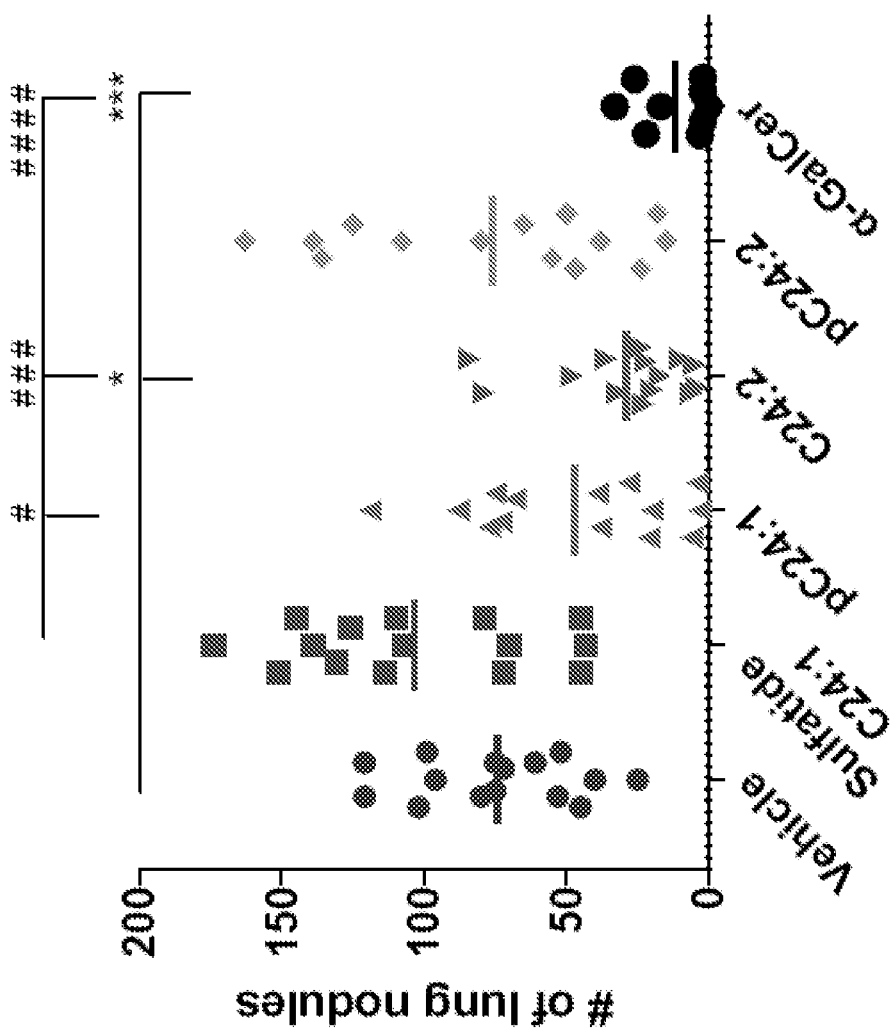

FIG. 5 shows the number of lung nodules observed for wild type (WT) BALB/c mice injected i.v. with $0.5 \times 10^6$ CT26 (colon cancer) cells and treated the same day with 33 nmol (about 30 μg) of sulfatide or sulfatide analogues or 500 pmol of α-GalCer injected intraperitoneally (i.p.) Lung nodules were counted 8 to 12 days after tumor inoculation according to the results in the monitored mice. n=10 from 2 independent experiments. * and #p≤0.05, *** and ###p≤0.001, ####p≤0.0001 by Kruskal-Wallis non-parametric multiple comparison test between analogues and vehicle (* symbols) and analogues and sulfatide (#symbols).

Figure 6:
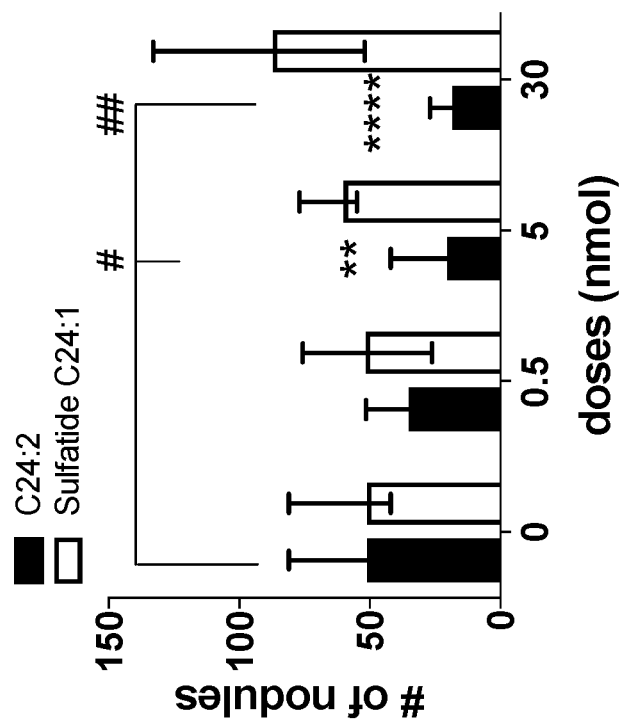

FIG. 6 is a graph showing the number of tumor nodules in mice following injection of sulfatide C24:1 or C24:2 at the indicated doses (nmol).

Figure 7:
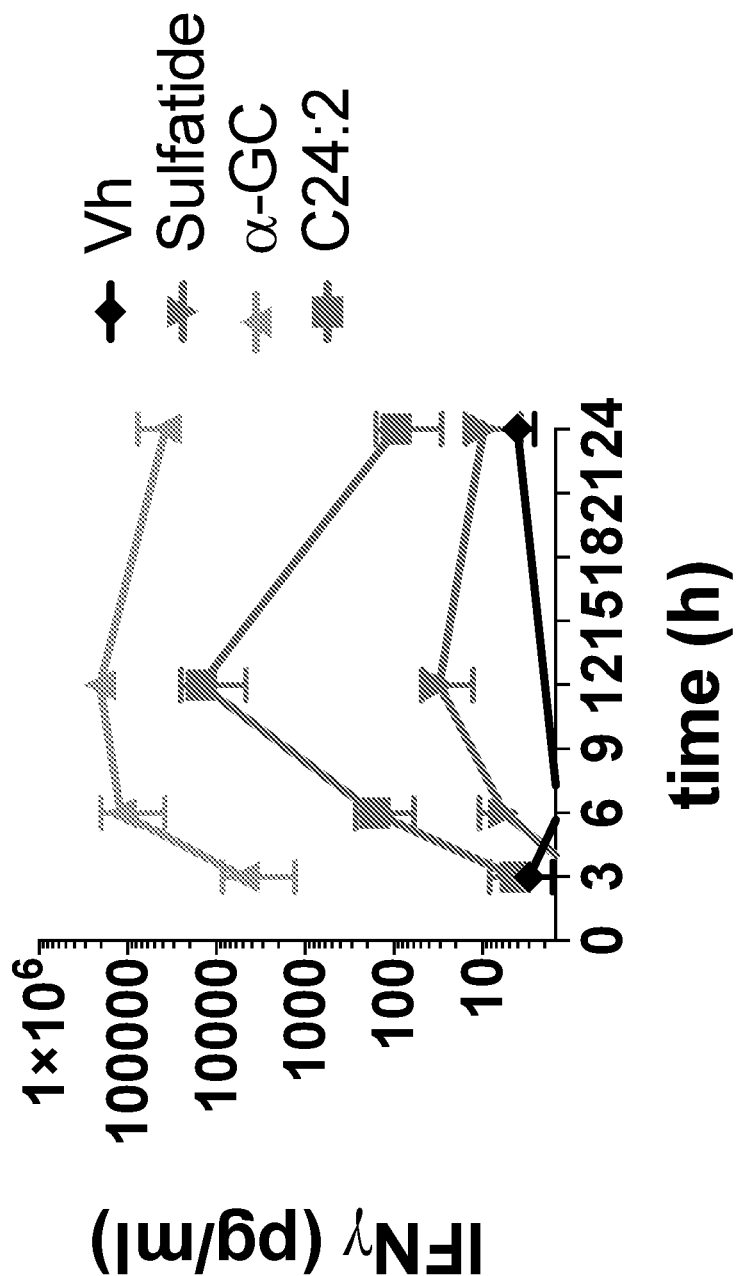

FIG. 7 is a graph showing the amount of interferon-gamma (IFN-γ) (pg/mL) measured in the serum of mice at the indicated number of hours following injection of sulfatide, alpha-GC, C24:2, or vehicle (Vh).

Figure 8B:
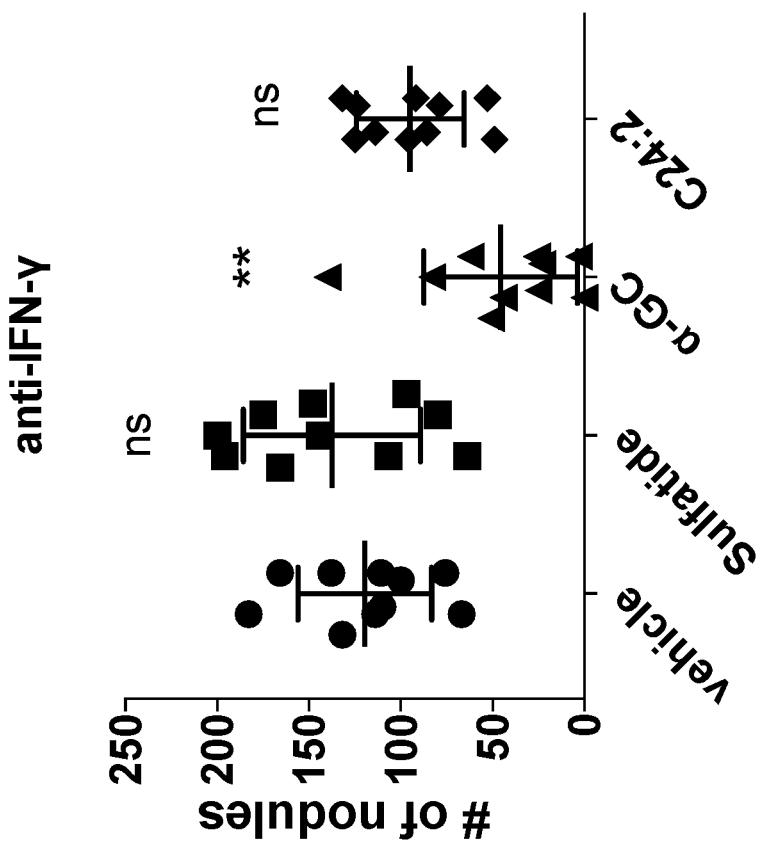
Figure 8A:
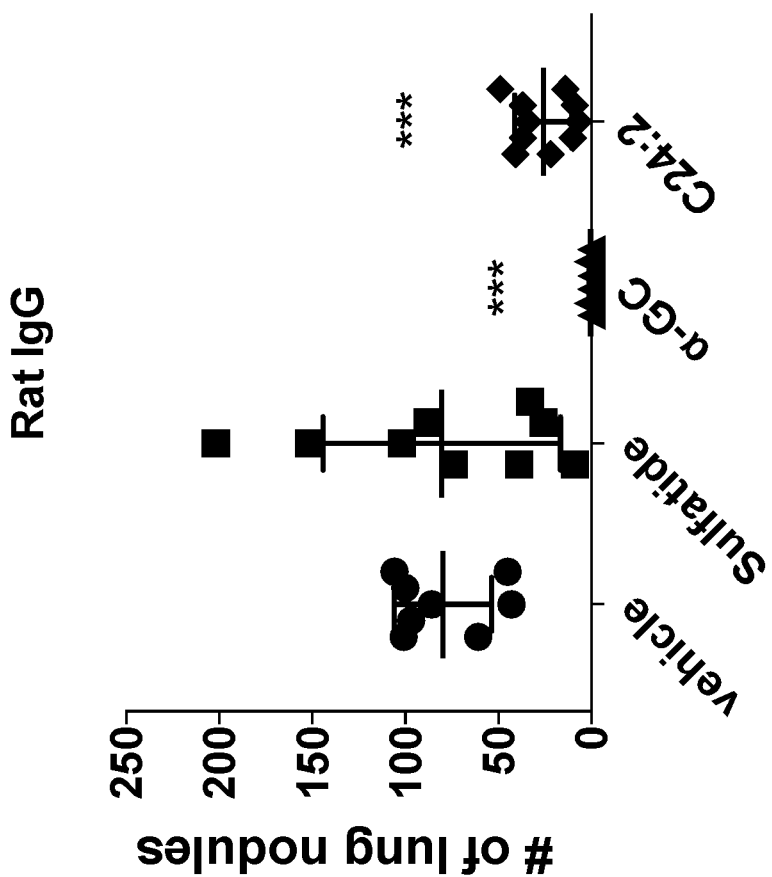

FIGS. 8A-8B are graphs showing the number of lung nodules in mice following treatment with sulfatide, alpha-GC, C24:2, or vehicle (Vh). Mice were injected with rat IgG isotype control (FIG. 8A) or anti-IFN-γ (FIG. 8B) on days 0, 1, 2, 3, and 5. n=10 animal per group from 2 independent experiments.  p≤0.01, *p≤0.001, by Man-Whitney non-parametric compared to vehicle.

DETAILED DESCRIPTION OF THE INVENTION

In an embodiment, the invention provides a compound of the formula (I) or (II):

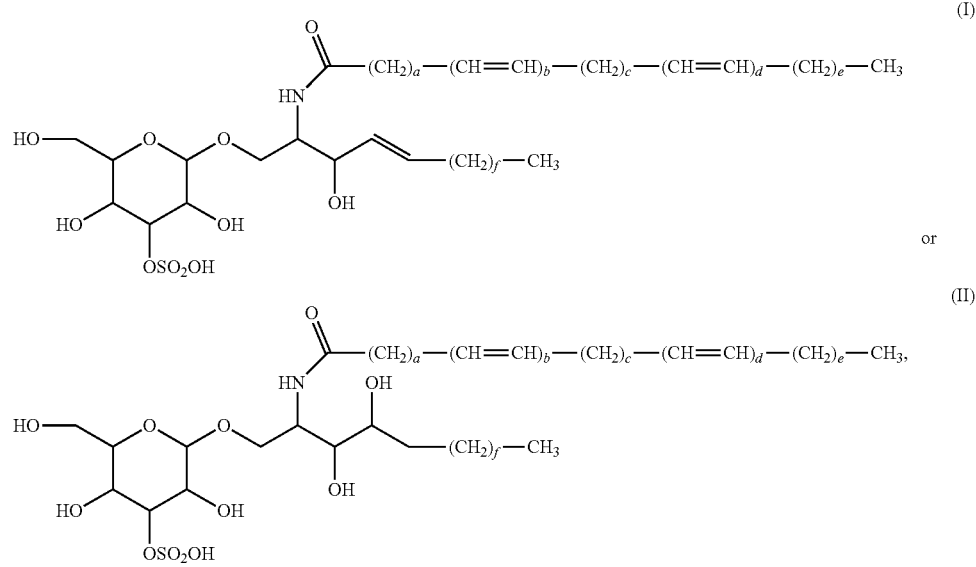

wherein a is an integer of from about 1 to about 20,
b is about 0 or about 1,
c is an integer of from about 1 to about 5,
d is about 0 or about 1,
e is an integer of from about 1 to about 10, and
f is an integer of from about 1 to about 20,
or a pharmaceutically acceptable salt thereof, solvate thereof, stereoisomer thereof, or mixture comprising stereoisomers thereof,
with the provisos that:
(i) when b is 1 and d is 0 in Formula (I), a+c+e≠20, and
(ii) when b and d are both 0 in Formula (II), a+c+e≠22 or 14.

In certain embodiments, a can be any integer from about 1 to about 20, e.g., a can be about 1, about 2, about 3, about 4, about 5, about 6, about 7, about 8, about 9, about 10, about 11, about 12, about 13, about 14, about 15, about 16, about 17, about 18, about 19, or about 20. In certain embodiments, a can be an integer of from about 2 to about 20, e.g., about 2 to about 18, about 2 to about 16, about 2 to about 14, about 5 to about 20, about 5 to about 18, about 5 to about 16, about 5 to about 14, about 10 to about 20, about 10 to about 18, about 10 to about 16, or about 10 to about 14. In certain preferred embodiments, a is about 13.

In certain preferred embodiments, b and d are both about 1.

In certain embodiments, e can be any integer from about 1 to about 10, e.g., a can be about 1, about 2, about 3, about 4, about 5, about 6, about 7, about 8, about 9, or about 10. In certain embodiments, e can be an integer of from about 2 to about 10, e.g., about 2 to about 8, about 2 to about 6, about 2 to about 4, about 3 to about 10, about 3 to about 8, about 3 to about 6, about 3 or to about 4. In certain preferred embodiments, e is about 4.

In certain embodiments, f can be any integer from about 1 to about 20, e.g., a can be about 1, about 2, about 3, about 4, about 5, about 6, about 7, about 8, about 9, about 10, about 11, about 12, about 13, about 14, about 15, about 16, about 17, about 18, about 19, or about 20. In certain embodiments, f can be an integer of from about 2 to about 20, e.g., about 2 to about 18, about 2 to about 16, about 2 to about 14, about 5 to about 20, about 5 to about 18, about 5 to about 16, about 5 to about 14, about 10 to about 20, about 10 to about 18, about 10 to about 16, or about 10 to about 14. In certain preferred embodiments, f is about 12.

In any of the above embodiments, the compound, salt, or solvate of formula (I) or formula (II) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess to 100% pure diastereomer).

It will be apparent to those of ordinary skill in the art that the compounds of formulas (Ib), (Ic), (IIb), and (IIc) comprise a galactose moiety linked to a sphingosine moiety or a phytosphingosine moiety in the β-configuration relative to the galactose ring. The absolute configuration of the galactose moiety of the compounds of formulas (Ib), (Ic), (IIb), and (IIc) is desirably the same absolute configuration as that of naturally occurring galactose. The artisan will also further understand that the compounds of formulas (Ib) and (Ic) comprise a sphingosine moiety and the compounds of formula (IIb) and (IIc) comprise a phytosphingosine moiety. The sphingosine moiety has a (2S,3R) configuration for the two asymmetric carbon atoms present therein and the phytosphingosine moiety has a (2S,3S,4R) configuration for the three asymmetric carbon atoms present therein.

In certain embodiments, the compound is of formula (I). In certain embodiments, the compound of formula (I) has the formula (Ia):

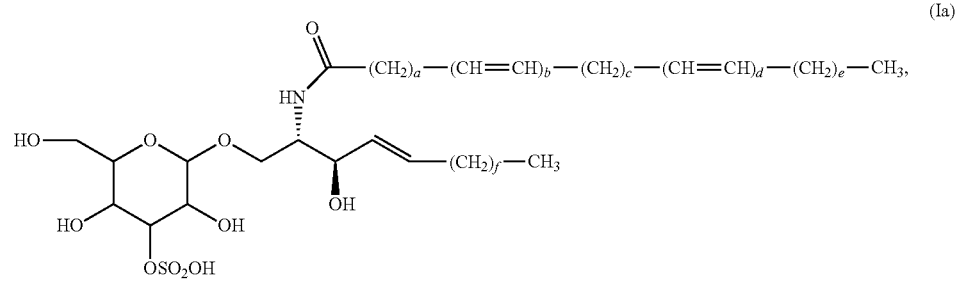

wherein a, b, c, d, e, and f are as described herein with respect to other aspects of the invention.

In certain preferred embodiments, the compound of formula (I) has the formula (Ib):

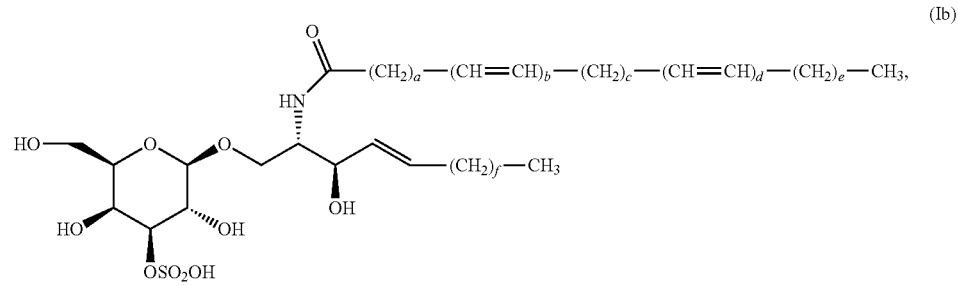

wherein a, b, c, d, e, and f are as described herein with respect to other aspects of the invention.

In a particular embodiment, the compound of formula (I) has the formula (Ic):

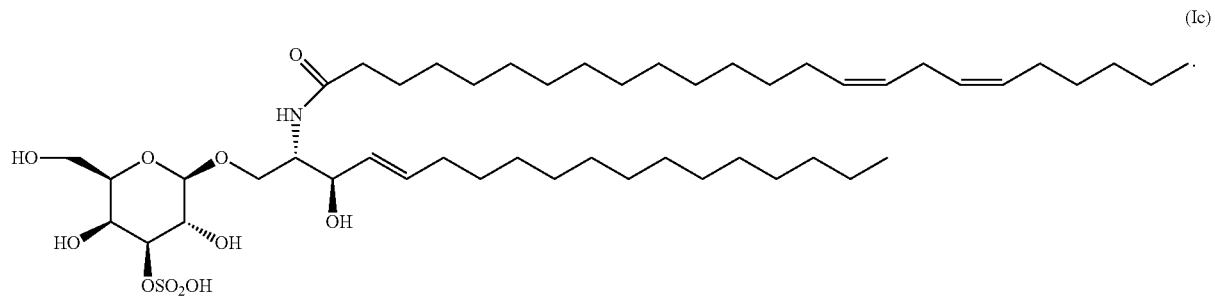

(Ic)

In certain embodiments, the compound is of formula (II). In certain embodiments, the compound of formula (II) has the formula (IIa):

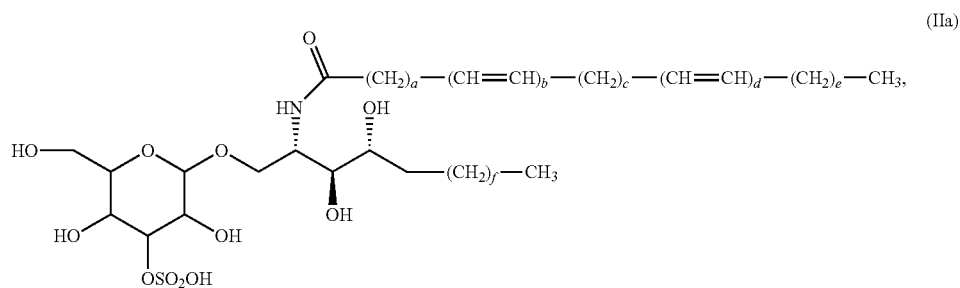

(IIa)

wherein a, b, c, d, e, and f are as described herein with respect to other aspects of the invention.

In certain preferred embodiments, the compound of formula (II) has the formula (IIb):

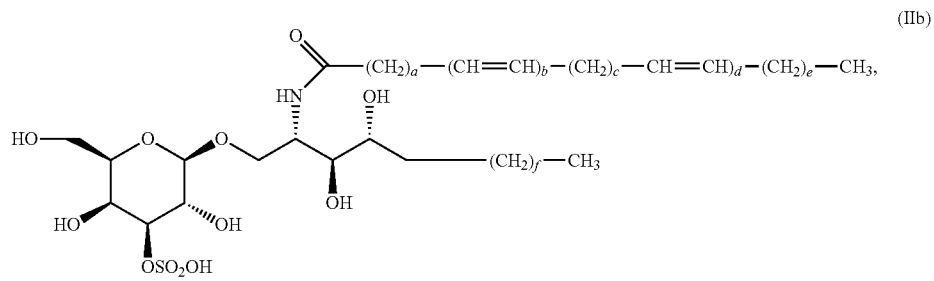

(IIb)

wherein a, b, c, d, e, and f are as described herein with respect to other aspects of the invention.

In a particular embodiment, the compound of formula (II) has the formula (IIc):

(IIc)

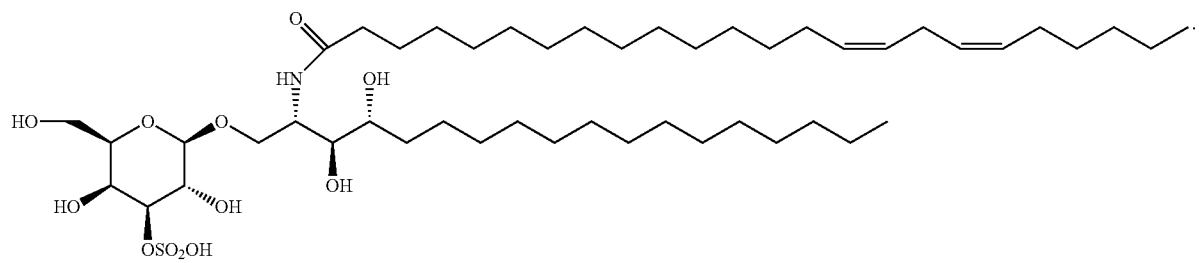

The phrase "pharmaceutically acceptable salt" is intended to include nontoxic salts synthesized from the parent compound which contains a basic or acidic moiety by conventional chemical methods. As will be appreciated by those of ordinary skill in the art, the compound of formula (I) and formula (II) contain an acidic proton as part of the sulfate moiety. Generally, such salts can be prepared by reacting the free acid forms of these compounds with a stoichiometric amount of the appropriate base in water or in an organic solvent, or in a mixture of the two. Generally, nonaqueous media such as ether, ethyl acetate, ethanol, isopropanol, or acetonitrile are preferred. Lists of suitable salts are found in *Remington: The Science and Practice of Pharmacy, 22$^{nd}$* Ed., Pharmaceutical Press (2012).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Preferred pharmaceutically acceptable salts of inventive compounds having an acidic moiety include sodium and potassium salts. The compounds of the present invention containing an acidic moiety are useful in the form of the free acid or in the form of a pharmaceutically acceptable salt thereof.

It should be recognized that the particular counterion forming a part of any salt of an embodiment of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

An embodiment of the present invention further provides a pharmaceutical composition comprising a compound as described above and a pharmaceutically acceptable carrier. An embodiment of the present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of embodiments of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical compositions of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The dose administered to a mammal, particularly, a human, in accordance with the present invention should be sufficient to effect the desired response. Such responses include reversal or prevention of the adverse effects of the disease (e.g., cancer) for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The therapeutically effective amount of the compound or compounds administered can vary depending upon the desired effects and the factors noted above. Typically, dosages will be between 0.01 mg/kg and 100 mg/kg of the subject's body weight, and more typically between about 0.05 mg/kg and 100 mg/kg, such as from about 0.1 to about 50 mg/kg, from about 0.1 to about 10 mg/kg, from about 0.1 to about 5 mg/kg, or from about 0.1 to about 1 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

The compositions described above can also include other immunostimulatory compounds. In an embodiment, the above compositions can also further comprise a therapeutically effective amount of an α-galactosylceramide or a salt or solvate thereof.

In an embodiment, the above compositions can also further comprise GM-CSF and/or one or more cytokines that induce cellular immunity. In some preferred embodiments, the one or more cytokines that induce cellular immunity comprises IL-12 and/or IL-15.

In an embodiment, the above compositions can also further comprise at least one T-cell co-stimulatory molecule selected from the group consisting of B7-1, B7-2, B7-3, B7-H, ICAM1, ICAM2, ICAM3, LFA1, LFA2, LFA3, CD40L, OX40L and 4-1BBL.

In an embodiment, the above compositions can also further comprise at least one Toll-like Receptor (TLR) ligand. In some preferred embodiments, the at least one TLR ligand is a ligand for a molecule selected from the group consisting of TLR2, TLR3, TLR4, TLR5, TLR7, TLR8, and TLR9.

In an embodiment, the above compositions can also further comprise a vaccine. In some preferred embodiments, the vaccine comprises one or more T cell receptor gamma alternate reading frame protein (TARP) peptides selected from the group consisting of 29-37-9V, 27-35, 1-20, 11-30, 21-40, 31-50 and 41-58 in combination with Sargramostin (GM-CSF) emulsified in Montanide ISA 51 VG.

In an embodiment, the above compositions can also further comprise an antibody. In some preferred embodiments, the antibody specifically binds to a molecule selected from the group consisting of CTLA-4, PD-1, and TGF-β.

In an embodiment, the present invention provides a method of selectively activating type II NKT cells in vitro, the method comprising culturing in vitro a mononuclear cell fraction comprising one or more mammalian type II NKT cells in the presence of a composition comprising a compound of the invention, salt thereof, solvate thereof, stereoisomer thereof, or mixture comprising stereoisomers thereof in an amount sufficient to activate mammalian type II NKT cells in vitro.

In another embodiment, the present invention provides a method of inducing an immune response, treating cancer, inhibiting growth of a tumor, or inhibiting metastasis of a tumor in a mammal in need thereof, comprising administering to the mammal a composition comprising a compound of the invention, salt thereof, solvate thereof, stereoisomer thereof, or mixtures comprising stereoisomers thereof in an amount effective to induce an immune response, treat cancer, inhibit growth of a tumor, or inhibit metastasis of a tumor in the mammal.

In yet another embodiment, the invention also provides a method of inhibiting a suppressive effect of type II NKT cells on the anti-cancer immune response in a mammal afflicted with the cancer, comprising administering to the mammal a composition comprising a compound of the invention, salt thereof, solvate thereof, stereoisomer thereof, or mixture comprising stereoisomers thereof in an amount effective to inhibit the suppressive effect of type II NKT cells on the anti-cancer immune response in the mammal.

In a further embodiment, the invention further provides a method of reducing a tumor burden in a mammal afflicted with a tumor, comprising administering to the mammal a composition comprising a compound of the invention, salt thereof, solvate thereof, stereoisomer thereof, or mixture comprising stereoisomers thereof in an amount effective to reduce the tumor burden in the mammal.

With respect to the inventive methods, the cancer or tumor can be any cancer or tumor, including that of any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer or tumor is that of the lung, colon, liver, breast, uterine cervix, and melanoma.

The activated type II NKT cells may be useful in treating or inhibiting the growth of tumors or cancer in a mammal, for example, in a lung of the subject.

It is also contemplated that type II NKT cells of a subject could be activated in vitro, and subsequently administered to the mammal for use in the treatment or inhibition of the growth or metastasis of a tumor, or cancer in the mammal. In particular, in an embodiment, the present invention provides a method of treating or inhibiting the growth or metastasis of a tumor or cancer in a subject comprising administering to the subject an effective amount of activated type II NKT cells which were prepared by culturing in vitro a mononuclear cell fraction, the cell fraction comprising one or more NKT cells in the presence of a compound of the invention, salt thereof, solvate thereof, stereoisomer thereof, or mixture comprising stereoisomers. The method of treatment of a tumor or cancer can also encompass culturing in vitro, a mononuclear cell fraction, the cell fraction comprising a one or more NKT cells in the presence of a compound of the invention, salt thereof, solvate thereof, stereoisomer thereof, or mixture comprising stereoisomers, and at least one or more T-cell co-stimulatory molecules. Further embodiments of the invention provide methods of inducing an immune response, treating cancer, inhibiting growth of a tumor, inhibiting metastasis of a tumor, inhibiting a suppressive effect of type II NKT cells on the anti-cancer immune response, and reducing a tumor burden in a mammal comprising administering to the mammal activated type II NKT cells prepared according to any of the methods described herein.

The term "treat," as well as words stemming therefrom, as used herein, does not necessarily imply 100% or complete treatment. Rather, there are varying degrees of treatment of which one of ordinary skill in the art recognizes as having a potential benefit or therapeutic effect. In this respect, the inventive methods can provide any amount of any level of treatment of cancer or tumor in a mammal. Furthermore, the treatment provided by the inventive method can include treatment of one or more conditions or symptoms of the cancer or tumor being treated. For example, treatment can include promoting the regression of a tumor.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Sulfatide-analogues reactive cells were identified in the lung of WT mice. These cells are also sulfatide-reactive type II NKT cells but distinct from type I NKT cells. All analogues induced the production of the regulatory cytokine IL-13 ex vivo. However, when used to stimulated type I and type II NKT hybridomas it appeared that the analogues with phytosphingosine chains activated both type I and type II NKT but without exhibiting major effect in vivo on the establishment of lung metastasis. On the contrary, one lipid revealed potentially promising clinical properties, the analogue C24:2. This analogue induced IL-13 production by lung cells. C24:2 was recognized only by a type II NKT TCR and not the prototypic type I NKT TCR and therefore activated only type II NKT cells and not type I. The strength of the lipid comes from its anti-tumor effect. In a model of lung metastasis induced by the i.v. injection of a colon cancer cell line, activated type II NKT cells were described to play a regulatory role reflected by an increased number of lung metastasis. It was also demonstrated that the well-described CD4$^+$CD25$^+$Foxp3$^+$ Tregs were not implicated in this effect but that the sulfatide-reactive type II NKT cells were the major population exerting a regulatory role in this model. The lipid C24:2, very unexpectedly and paradoxically induced a significant reduction of the number of lung nodules. Lung metastases are extremely frequent and resistant to standard treatment. Thus, any mechanism that could control the regulatory activity of lung type II NKT may be useful for the treatment of cancer, e.g., lung metastases. The anti-tumor effect of C24:2 may be sufficient on its own, but even if not strong enough as a single agent in its present form as a therapeutic, the lipid C24:2 could be used in combination therapies or as an adjuvant to enhance the efficacy of other anti-tumor immunotherapies.

Chemistry

The inventive compounds can be synthesized as described in Example 5 for representative embodiments. Scheme 1 depicts a preparation of α-GalCer precursor of sulfatide C24:2 in accordance with an embodiment of the invention. Scheme 2 depicts a preparation of 15Z,18Z-Tetracosadienoic acid (13) side chain fragment in accordance with an embodiment of the invention. Scheme 3 depicts a synthesis of α-GalCer precursors (19a/19b) of sulfatides pC24:2 and pC24:1 in accordance with an embodiment of the invention.

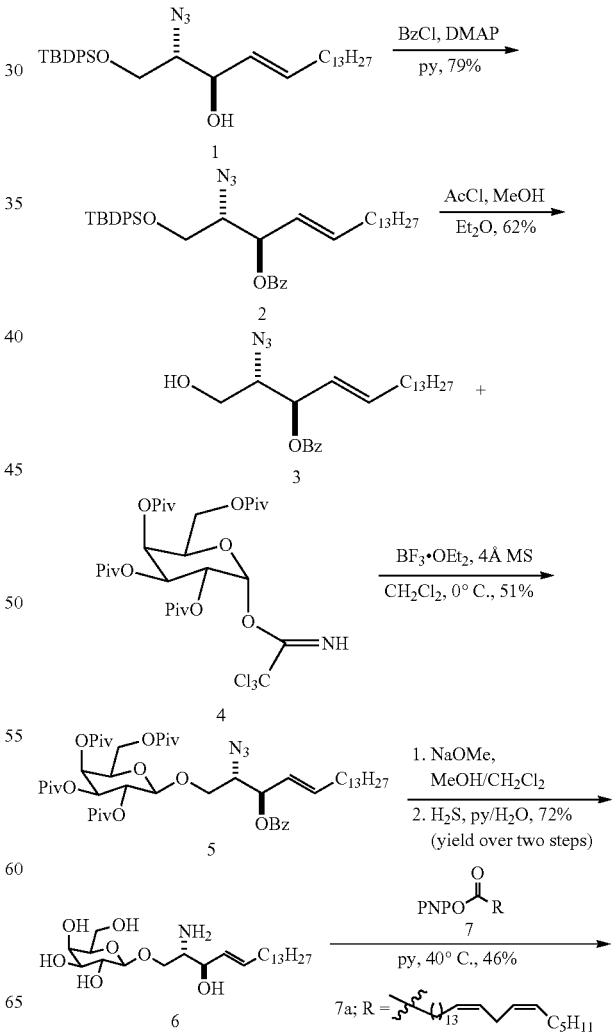

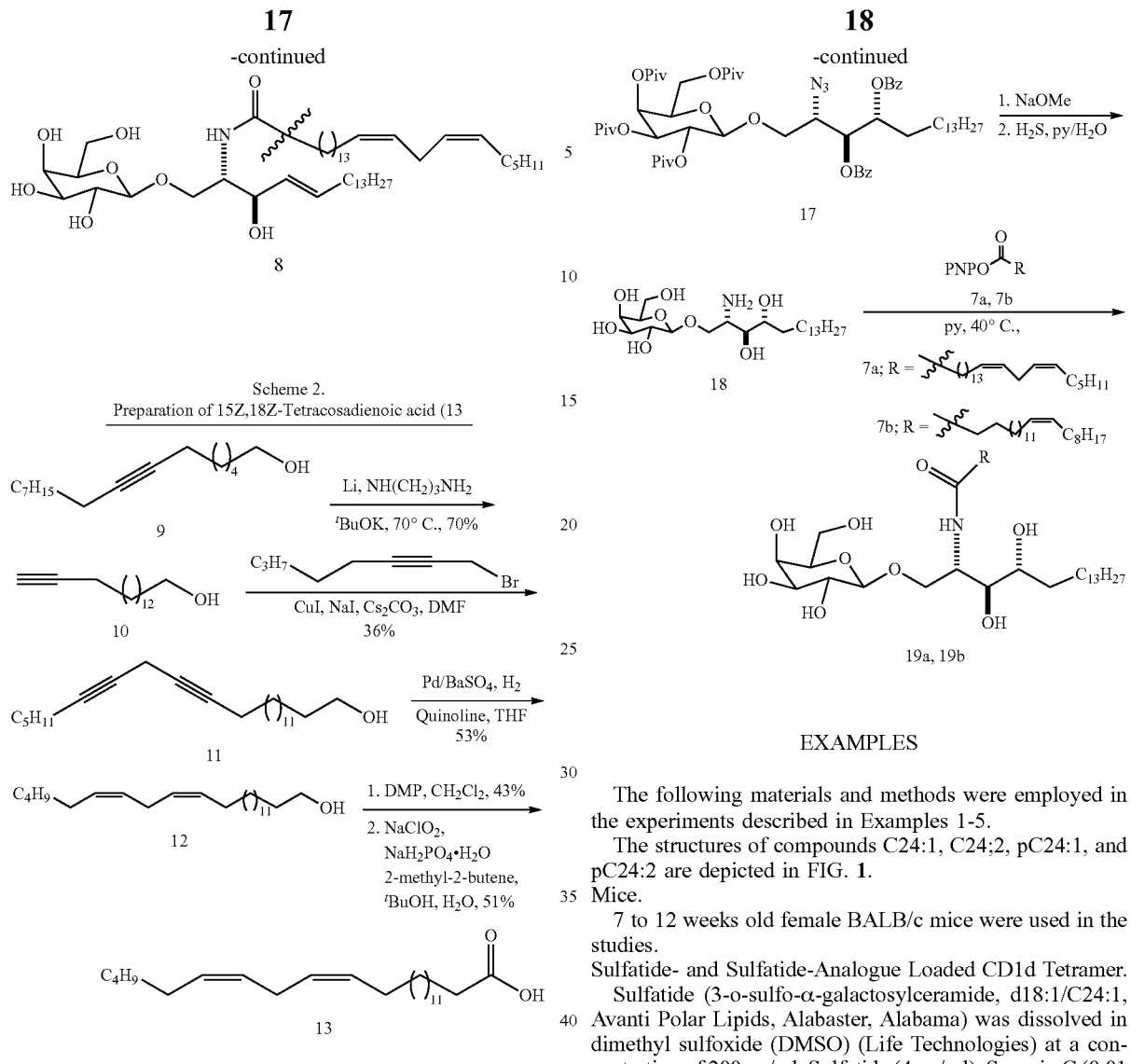

EXAMPLES

The following materials and methods were employed in the experiments described in Examples 1-5.

The structures of compounds C24:1, C24;2, pC24:1, and pC24:2 are depicted in FIG. 1.

Mice.

7 to 12 weeks old female BALB/c mice were used in the studies.

Sulfatide- and Sulfatide-Analogue Loaded CD1d Tetramer.

Sulfatide (3-o-sulfo-α-galactosylceramide, d18:1/C24:1, Avanti Polar Lipids, Alabaster, Alabama) was dissolved in dimethyl sulfoxide (DMSO) (Life Technologies) at a concentration of 200 µg/ml. Sulfatide (4 µg/ml), Saposin C (0.01 µg/ml) and mouse-CD1d (mCD1d) monomers (8 µg/ml) (NIH tetramer core facility, Emory University, Atlanta, GA) were mixed in sodium acetate buffer (50 mM, pH 5.0) in a glass vial. After incubation at 37° C. overnight, the acidic buffer was replaced with DPBS, using Amicon Ultra Centrifugal Filter Units 30K (Millipore, Darmstadt, Germany). BV421-conjugated streptavidin (Biolegend, San Diego, CA) was added and incubated at room temperature. The total amount of streptavidin was a quarter mole per mole of mCD1d monomers, and one sixth part of total amount was added every 10 minutes.

Cells.

The hybridoma cell line DN32.D3 created by Brutkiewicz et al. (R. R. Brutkiewicz et al., *J. Experimental Medicine*, 183: 1913-1919 (1995)) that express the TCR semi-invariant α-chain Vα14Jα18 associated with the Vβ8.2Jβ2.4 chain was used.

The hybridoma XV19 was created by Cardell, S. et al. (*J. Experimental Medicine*, 182: 993-1004 (1995)) and was provided by Susanna Cardell.

For the preparation of lung mononuclear cells, lungs were perfused with warm Dulbecco's Phosphate-Buffered Saline (DPBS) (Life Technologies, Frederick, MD) from the heart right ventricle. Single cell suspension was prepared with a Lung Dissociation Kit (Miltenyi Biotec, San Diego, CA)

according to the manufacturer's protocol. Lung mononuclear cells (LMNC) were then purified from the cell suspension by a 40%/80% gradient of Percoll (Sigma-Aldrich, St-Louis, MO).

Differentiation of Bone-Marrow Derived Dendritic Cells (BDMC).

BMDC were prepared by collecting bone marrow cells from femurs and tibias of BALB/c mice in complete medium. Cells were suspended at the concentration of $0.2 \times 10^6$/ml in complete medium supplemented with 20 ng/ml of GM-CSF (Peprotech, Rocky Hill, NJ) and $2 \times 10^6$ cells were plated per Petri dish (Corning, Tewksbury, MA). Fresh medium supplemented with 20 ng/ml GM-CSF was added at day 3 and refreshed at day 6. At day 8 the cells were harvested, washed in complete medium and suspended at $0.4 \times 10^6$/ml in complete medium supplemented with 10 ng/ml of GM-CSF and 1 µg/ml of LPS (Sigma-Aldrich). $4 \times 10^6$ cells were plated per Petri dish for 24 h.

Ex Vivo Stimulation of Lung Mononuclear Cells.

200 µg of sulfatide of sulfatide-analogues dry powder was dissolved in 100 µl of DPBS containing 0.5% Tween20 (PBS-Tween) (Avantor performance materials). BMDCs were washed and put at the concentration of $1 \times 10^7$/ml and incubated 3 h at 37° C. in presence of 30 µg/ml of sulfatide or sulfatide-analogues or the same volume of PBS-Tween as vehicle control. After washing, $100 \times 10^3$ pulsed BMDCs were cultured with $0.5 \times 10^6$ lung mononuclear cells in complete medium in flat-bottom 96 well plates for 4 days at 37° C., 5% $CO_2$. When indicated, 10 µg/ml of anti-CD1d antibody (20H2, Harlan, Indianapolis, IN) was added. Supernatants were harvested, and IL-13 production was determined by ELISA according to the recommendations of the manufacturer (eBioscience).

In Vitro Stimulation of NKT Hybridoma Cell Lines.

CD monomers were loaded as described above. Flat bottom 96 well plates were coated overnight with 0.5 µg of CD1d monomers loaded with 4 µM of sulfatide or sulfatide-analogues, 10 nM of α-GalCer or with 10 ng/ml of anti-CD3 antibody (Biolegend, San Diego, CA) dissolved in PBS. Plates were then washed in PBS and complete medium. $50 \times 10^3$ hybridoma cells in 200 µl of complete medium were plated in presence or not of anti-CD1d blocking antibody 20H2.

Cells were cultured for 24 h at 37° C., 5% $CO_2$. The production of IL-2 was measured by ELISA from the culture supernatant according to the recommendations of the manufacturer.

Lipid Preparation for In Vivo Treatment.

200 µg of sulfatide of sulfatide-analogues dry powder were resuspended with 40 µl of PBS-Tween20-0.05% and warm at 37° C. for 10 min. Then, 697 µl of DPBS were added to obtain a concentration of 300 µg/ml of lipid. Mice received an i.p injection of 100 µl of sulfatide or analogue mix that is equivalent to 30 µmol of lipid. A solution of 500 µM of α-GalCer in DPBS-tween20-0.05% was thawed and sonicated at 60° C. for 2 min and a solution at 10 µM was prepared in in DPBS. Mice were injected i.p. with 10 nmol (100 µl) of α-GalCer solution.

Tumor Model and Treatment.

The CT26 cell were cultured in tumor medium: RPMI 1640 (Life technologies) supplemented with 10% heat inactivated fetal calf serum, 2 mM L-Glutamine, penicillin, streptomycin, 10 mM HEPES, 1/100 vol non-essential amino acids, and 1 mM sodium pyruvate 1/1000 of β-mercaptoethanol. Cells were harvested at 80-85% confluence, detached from plastic with trypsin treatment and resuspended at $5 \times 10^6$ cell/ml in DPBS. Mice were injected i.v in the tail vein with $0.5 \times 10^6$ CT26 cells (100 µl). The same day, mice were injected i.p. with 30 µmol of sulfatide or sulfatide analogues, or 10 nmol of α-GalCer.

Example 1

This example demonstrates the identification of sulfatide analogue-specific cells in mouse lung.

It has been previously shown that sulfatide-loaded tetramer could be used to identify sulfatide-reactive type II NKT cells in the lungs of mice. Live lung mononuclear cells from BALB/c mice were stained with pC24:1-, pC24:2-, C24:2- and C24:1-loaded CD1d tetramer along with α-GalCer-loaded CD1d tetramer and anti-TCRβ and anti-CD45 antibodies using a negative gate. The results are shown in FIG. 2.

Figure 1A:
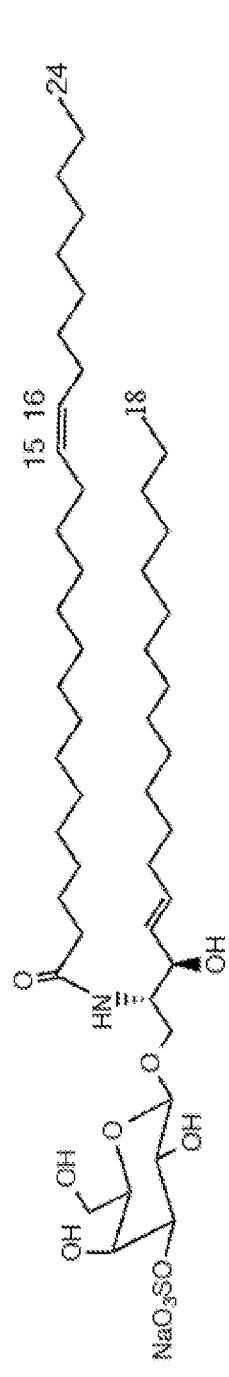
FIG. 1A shows the structure of the compounds sulfatide-C24:1, pC24:1, and pC24:2.
Figure 1A:
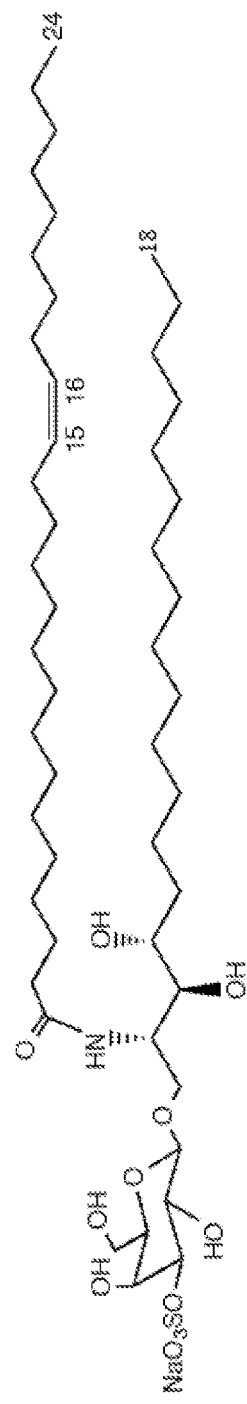
Figure 1A:
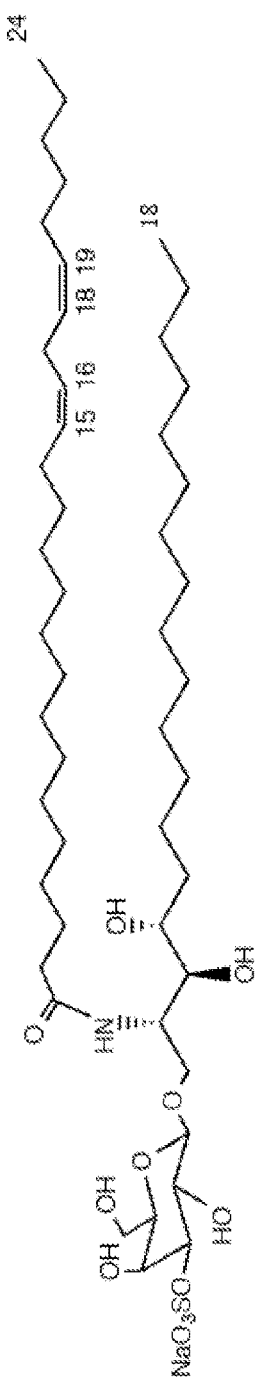
Figure 1B:
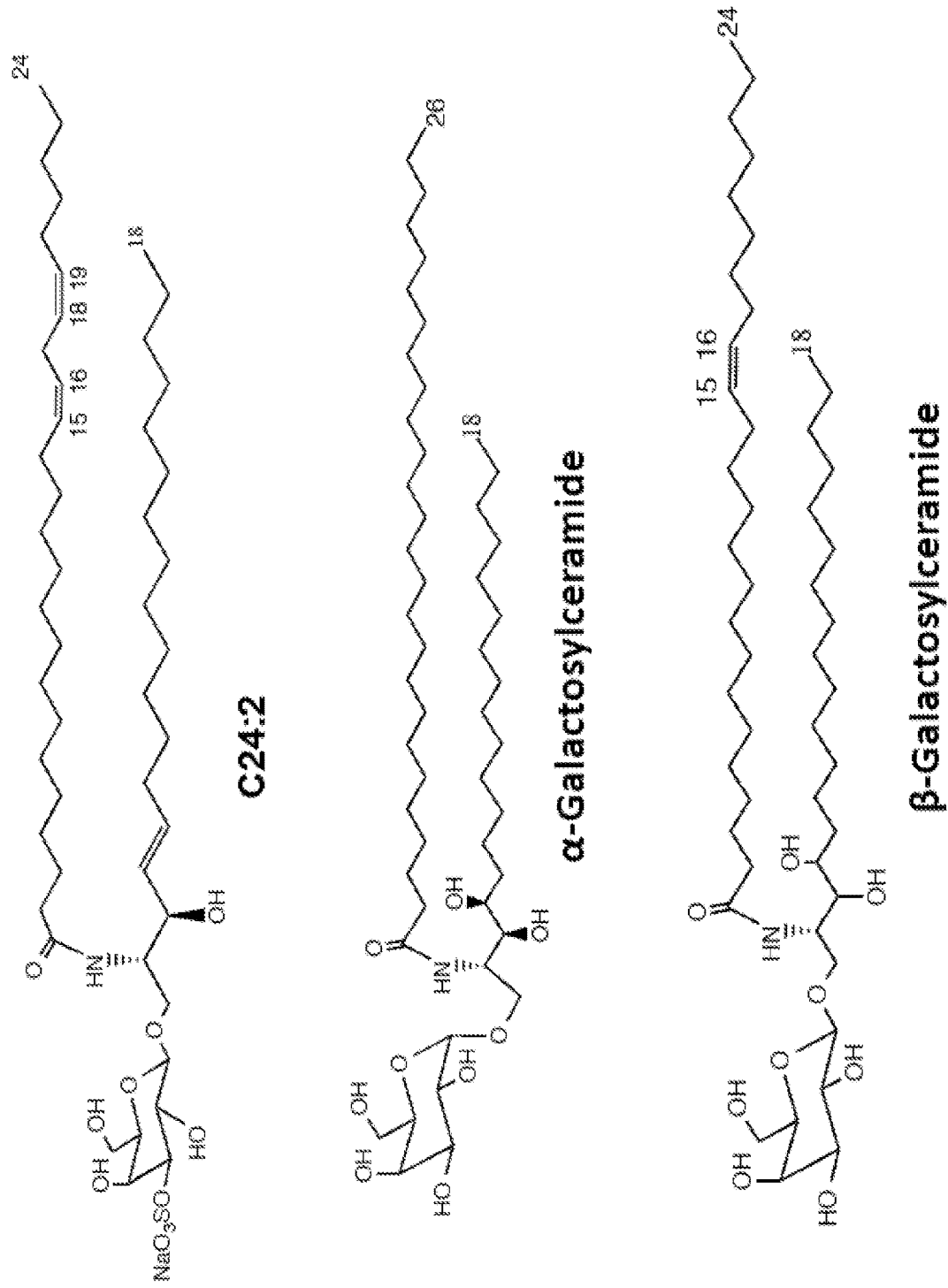
FIG. 1B shows the structure of the compounds C24:2, α-galactosylceramide, and β-galactosylceramide.
Figure 2:
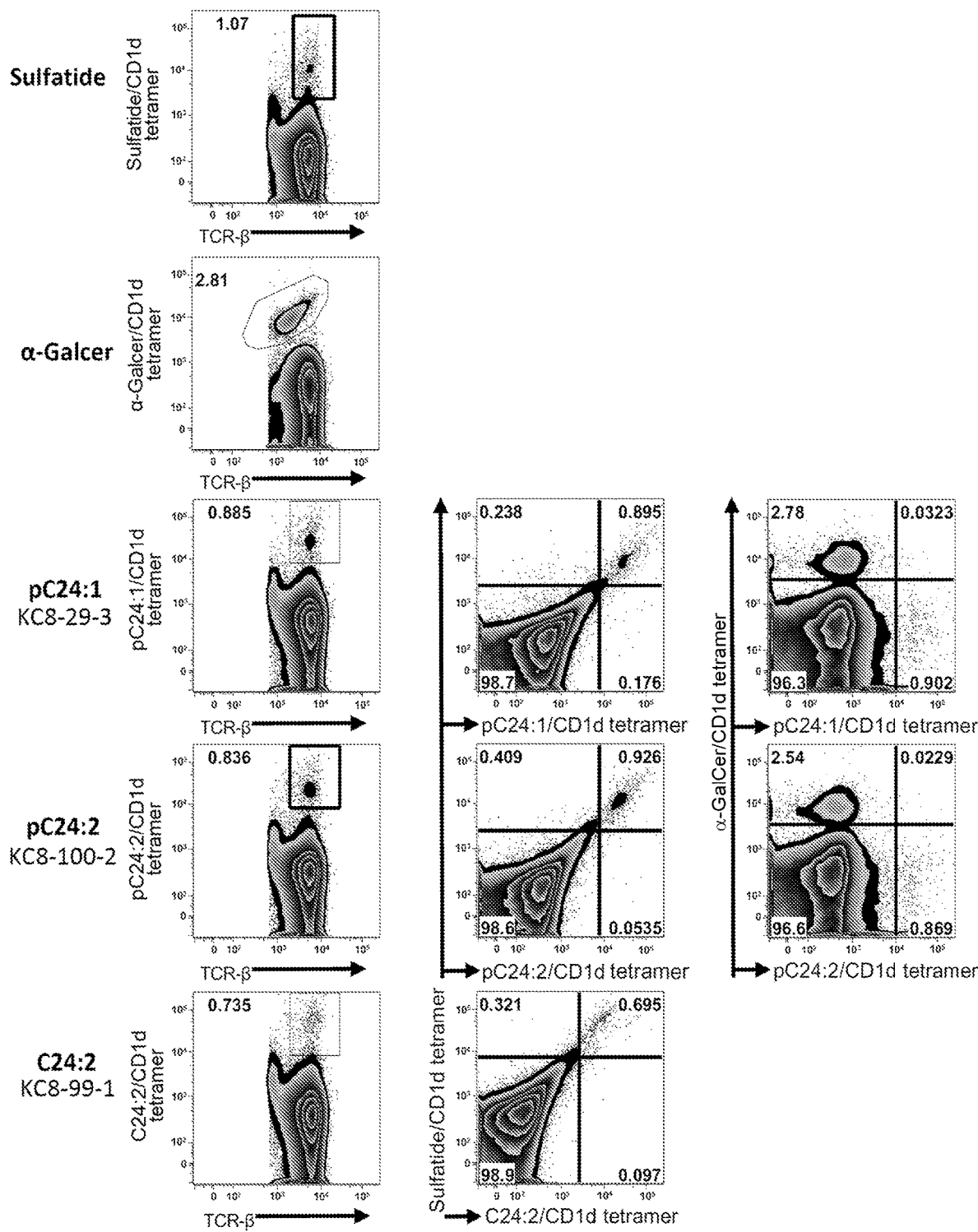
FIG. 2 shows flow cytometry data of lung cells stained with sulfatide-analogue loaded CD1d tetramer and triple stained with sulfatide-loaded and α-GalCer CD1d tetramer. Numbers indicates the percentage of cells in the gate.

Thus, lung cells were stained with sulfatide-analogue loaded-CD1d tetramer and sulfatide-analogue specific cells in the lungs were identified (FIG. 2. 2 left panels). A triple staining with sulfatide-loaded and α-GalCer CD1d-tetramer revealed that sulfatide-analogue specific cells were also sulfatide-specific (FIG. 2. 2 middle panels) but totally distinct from the α-GalCer-specific type I NKT cells. These results showed that the identified analogue specific cells are type II NKT cells and distinct from type I NKT cells.

Example 2

This example demonstrates that the sulfatide analogues pC24:1, pC24:2, and C24:2 induce IL-13 production in lung mononuclear cells.

Lung mononuclear cells from WT BALB/c mice were stimulated for 4 days in presence of BMDC (bone marrow derived dendritic cells) pulsed with 33 µM of sulfatide, vehicle control, or 33 µM of the sulfatide analogues pC24:1, pC24:2, or C24:2 in presence or absence of the anti-CD1d blocking antibody 20H2 to confirm the dependency of the IL-13 production on CD1d. The production of IL-13 was measured by ELISA in the culture supernatant. The results are shown in FIG. 3 (n=4, duplicates from 2 independent experiments.

Figure 3:
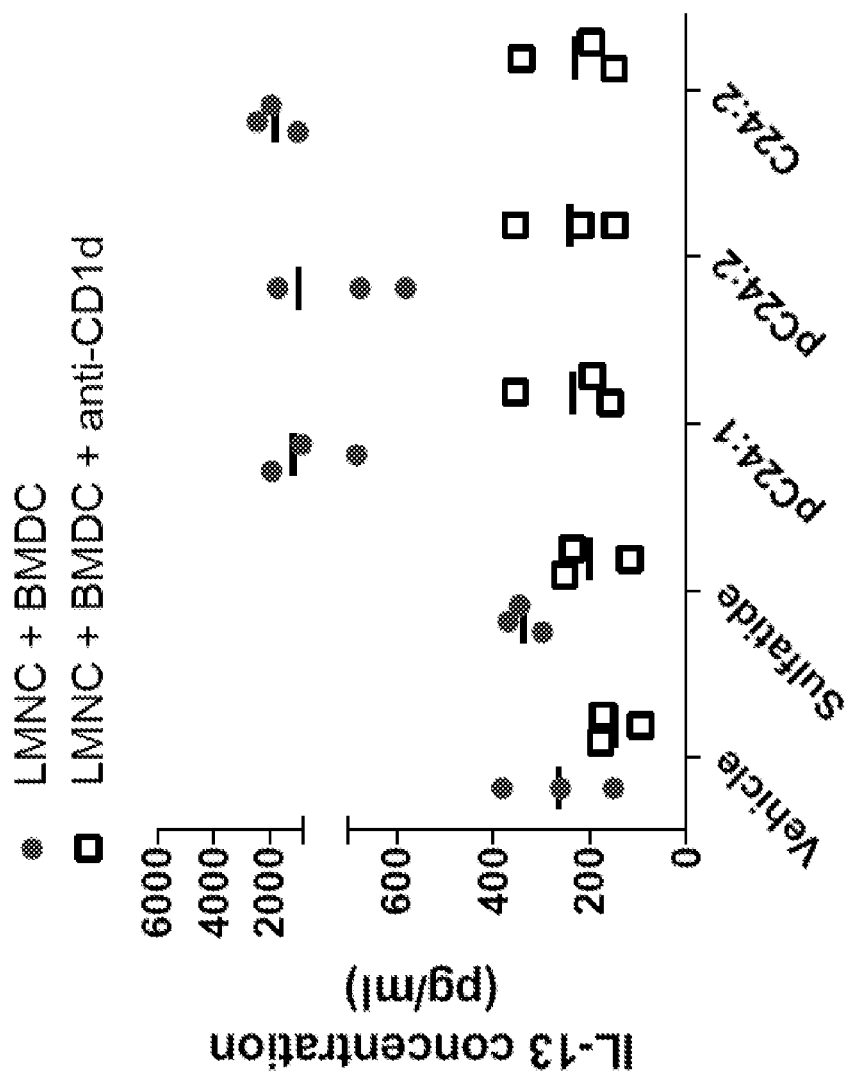
FIG. 3 shows IL-13 concentrations produced by lung mononuclear cells (LMNC) and bone marrow-derived dendritic cells (BMDC) pulsed with sulfatide or sulfatide analogues in the presence or absence of blocking anti-CD1d antibody.

As is apparent from the results shown in FIG. 3, all of pC24:1, pC24:2, and C24:2 induced a high production of IL-13 that was also abrogated in the presence of anti-CD1d blocking antibody and is therefore dependent upon the interaction of NKT TCR with the complex sulfatide-analogue/CD1d expressed by the BMDC.

Example 3

This example demonstrates that the structure of the ceramide portion of the sulfatide analogues influenced the differential activation of type I and type II hybridomas.

The sorting of lung type I and type II NKT cells is a very long and complicated process that does not allow the recovery of enough cells to do reliable experiments in vitro. Therefore, well-described type I and type II NKT hybridoma cell lines were used in this experiment. The type I NKT hybridoma DN32.D3 expresses the murine semi-invariant TCR Vα14Jα18 associated with the Vβ8.2/Jβ2.4 chain (Brutkiewicz et al.) and is specific for α-GalCer. The type II NKT hybridoma XV19 expresses the TCR chain Vα1/Jα26 associated with the β-chain Vβ16/Jβ2.1, and is described to be specific for sulfatide and does not respond to α-GalCer (Cardell et al.). Because XV19 was shown to be autoreactive to spleen cells used as APC (Cardell et al.), the 2 clones were stimulated with plate coated CD1d monomers loaded with lipids or vehicle as negative control for 24 h using IL-2 production as a read-out of activation. The results are shown in FIGS. 4A-4B. The results are summarized in Table 1.

TABLE 1

|  | XV19 | DN32 |
|---|---|---|
| Sulfatide C24:1* | +* | — |
| pC24:1*** | +*** | +*** |
| C24:2* | +* | — |
| pC24:2*** | +*** | +*** |
| α-GalCer** | — | ++** |
| β-GalCer** | — | +** |

*lipids activating only type II NKT hybridoma
**lipids activating only type I NKT hybridoma
***lipid activating both hybridomas As a positive control of activation, cells were also stimulated with plate bound anti-CD3 antibody. XV19 was activated by sulfatide-C24:1 but not α-GalCer or β-GalCer and DN32.D3 was activated by α-GalCer and β-GalCer but not sulfatide-C24:1. The analogues pC24:1 and pC24:2 activated XV19, inducing a production of IL-2 in an amount similar to sulfatide C24:1, but also activated DN32.D3. The level of activation (i.e. amount of IL-2 produced) of the DN32.D3 cells with pC24:1 and pC24:2 was lower than that induced by α-GalCer and in the same range as the one induced by β-GalCer. Interestingly, C24:2, similar to sulfatide-C24:1 activated only XV19 and not DN32.D3. The IL-2 production induced by the lipids was CD1d-dependent in all the conditions because it was abrogated in presence of the anti-CD1d blocking antibody.

Example 4

This example demonstrates that the Type II NKT specific sulfatide analogue C24:2 reduced the development of lung metastasis in vivo.

It has been previously demonstrated that in vivo injection of sulfatide in a murine model of lung metastasis increased the development of nodules whereas α-GalCer abrogated it (Ambrosino, E. et al., *J. Immunology*, 179: 5126-5136 (2007)). Using the same model, the impact of the sulfatide-analogues was tested on the establishment of lung metastasis.

WT BALB/c mice were injected intravenously (i.v.) with $0.5 \times 10^6$ CT26 (colon cancer) and treated the same day with 33 nmol of sulfatide or sulfatide-analogues or 500 pmol of α-GalCer injected i.p. Lung nodules were counted 8 to 12 days after tumor inoculation according to the results in the monitoring mice. n=10 from 2 independent experiments. The results are shown graphically in FIG. 5.

It was confirmed that sulfatide-C24:1 increased the number of lung nodules whereas α-GalCer inhibited their development. Despite their capacity to activate the type I NKT hybridoma DN32.3, pC24:1 and pC24:2 did not have any effect on the development of lung nodules compared to vehicle. Very interestingly and paradoxically, the lipid C24:2, described in this work as specific for type II NKT cells nevertheless significantly reduced the number of lung nodules compared to both vehicle and sulfatide.

Example 5

This example demonstrates the synthesis of compounds, in accordance with an embodiment of the invention.

Tetrahydrofuran (THF) was dried using a solvent dispensing system (SDS) with a column of neutral alumina. Pyridine, toluene, dimethylformamide (DMF), methylene chloride ($CH_2Cl_2$), deuterated chloroform ($CDCl_3$), methanol (MeOH), deuterated methanol and ethanol (EtOH) were dried over 4 Å molecular sieves (MS).

N-tert-BOC-L-serine and hexacosanoic acid were purchased from Novabiochem and TCI, respectively. The other reagents were purchased from Acros, Alfa Aesar or Aldrich and used without further purification.

All reactions were conducted under an atmosphere of $N_2$ in glassware that had been dried overnight in an oven at 120° C. Where appropriate, control of the reaction temperature was achieved with a solid $CO_2$/acetone bath, an ice bath or a heated oil bath.

$^1H$ NMR spectra were recorded at 500 MHz, 400 MHz and/or 300 MHz and calibrated to the residual $CHCl_3$ peak in $CDCl_3$ at 7.26 ppm, to the TMS peak at 0.0, or to the residual MeOH peak in MeOD at 3.34 ppm. $^{13}C$ NMR spectra were recorded at 125 MHz, 100 MHz, and/or 75 MHz and calibrated to the residual $CHCl_3$ peak in $CDCl_3$ at 77.23, or to the residual MeOH peak in MeOD at 49.5 ppm. The following abbreviations are used for peak multiplicities: app (apparent), s (singlet); br s (broadened singlet); d (doublet); dd (doublet of doublet); ddd (doublet of doublet of doublets); dddd (doublet of doublet of doublet of doublets); dt (doublet of triplets); tt (triplet of triplets) t (triplet); q (quartet); quin (quintet); m (multiplet). Coupling constants, J, are reported in Hertz (Hz).

IR spectra were recorded on a Brucker FT-IR spectrometer. High-resolution mass spectra (HiRMS) were obtained on an AccuTOF instrument equipped with a DART ionization source.

Melting points were observed in open Prex capillary tubes and are uncorrected. Specific rotations $[\alpha]_D$ were obtained on a JASCO polarimeter using the sodium D-line as a source, and the concentration (c) is expressed in g per 100 mL.

Flash chromatography was performed on Silica Gel, 40 micron, 32-63 flash silica from Sorbent. Thin layer chromatography was performed on silica gel (Silicycle Silica Gel 60 $F_{254}$ glass plates). Compounds were visualized by UV, 5% phosphomolybdic acid in ethanol, 0.5% potassium permanganate in water or a solution of ethanol/$H_2SO_4$/AcOH/p-anisaldehyde (135:5:1.5:3.7). Ceric molybdate in a solution of $H_2O$/ammonium molybdate/ceric ammonium molybdate/$H_2SO_4$ (235 mL: 12 g: 0.5 g: 15 mL) was used for sulfatides.

(2S,3R,4E)-2-Azido-(3-benzoyloxy-1-tert-butyldiphenylsilyloxy)octadec-4-ene (2)

BzCl (2.3 mL, 20 mmol) was added to a solution of (2S,3R,4E)-2-azido-1-(tert-butyldiphenylsilyloxy)octadecen-3-ol (1) (Kim, S. et al., *J. Org. Chem.* 2006, 71, 8661) (2.70 g, 4.91 mmol) and DMAP (90 mg, 0.74 mmol) in pyridine (43 mL). The reaction mixture was stirred overnight. Ice-cold $H_2O$ (50 mL) was added, and the solution was extracted with $CH_2Cl_2$ (3×30 mL). The combined organic layers were dried ($MgSO_4$), filtered and concentrated. Flash column chromatography purification of the crude product on silica gel (petroleum ether/EtOAc, 95:5) gave 2 (2.51 g, 79%) as a slightly yellow oil: $^1H$ NMR (400 MHz, $CDCl_3$) δ 8.01 (dd, J=8.0, 0.9 Hz, 2H), 7.69-7.64 (m, 4H), 7.57 (dt, J=6.9, 1.6 Hz, 1H), 7.46-7.37 (m, 6H), 7.35-7.31 (m, 2H), 5.89 (dt, J=15.1, 6.7 Hz, 1H), 5.67 (dd, J=7.9, 4.8 Hz, 1H), 5.51 (dd, J=15.4, 8.0 Hz, 1H), 3.85-3.81 (m, 1H), 3.78-3.74 (m, 2H), 2.02 (dt, J=7.0, 7.0 Hz, 2H), 1.33-1.24 (m, 22H), 1.08 (s, 9H), 0.89 (t, J=7.0 Hz, 3H); $^{13}$C NMR (100 MHz, CDCl$_3$) δ 165.4, 138.7, 135.8, 133.3, 133.1, 132.9, 130.3, 130.1, 130.0, 130.0, 128.6, 128.0, 128.0, 123.4, 74.5, 66.0, 63.6, 32.5, 32.1, 29.9, 29.8, 29.6, 29.6, 29.3, 28.9, 26.9, 22.9, 19.3, 14.4.

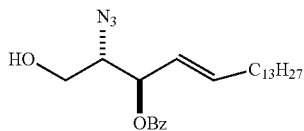

(2S,3R,4E)-2-Azido-3-(O-benzoyl)octadec-4-en-1-ol (3)

AcCl (0.75 mL, 10.5 mmol) was added drop-wise to MeOH (19 mL) at 0° C. (2S,3R,4E)-2-azido-(3-benzoyloxy-1-tert-butyldiphenylsilyloxy)octadec-4-ene (2) (0.37 g, 0.57 mmol) in Et$_2$O (19 mL) was added to the in situ generated HCl solution (Nashed, E. M. et al., *J. Org. Chem.* 1987, 52, 5255). The reaction solution was stirred for 2 d. Saturated aqueous NaHCO$_3$ was added. The two layers were separated, and the aqueous layer was extracted with CH$_2$Cl$_2$ (3×25 mL). The combined organic layers were dried (MgSO$_4$), filtered and concentrated. The crude product was purified by flash column chromatography on silica gel (petroleum ether/EtOAc, 90:10) to give 3 (0.15 g, 62%) as slightly yellow oil. (Compostella, F. et al., *Tetrahedron Asymmetry* 2002, 13, 867)$^1$H NMR (400 MHz, CDCl$_3$) δ 8.07-8.05 (m, 2H), 7.60-7.56 (m, 1H), 7.45 (t, J=7.8 Hz, 2H), 6.01-5.91 (m, 1H), 5.64-5.58 (m, 2H), 3.82-3.73 (m, 2H), 3.63 (ddd, J=11.6, 6.9, 4.6 Hz, 1H), 2.11-2.03 (m, 3H), 1.42-1.35 (m, 2H), 1.32-1.25 (m, 20H), 0.88 (t, J=7.0 Hz, 3H). $^{13}$C NMR (100 MHz, CDCl$_3$) δ 165.7, 139.0, 133.5, 130.0, 130.0, 128.7, 123.5, 74.8, 66.4, 62.2, 32.6, 32.1, 29.9, 29.8, 29.6, 29.6, 29.3, 28.9, 22.9, 14.3.

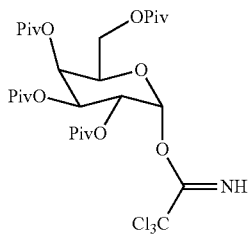

(2,3,4,6-Tetra-O-pivaloyl-α-D-galactopyranoside)-1-trichloroacetimidate (4)

DBU (0.86 mL, 5.74 mmol) was added drop-wise to a stirred solution of (2,3,4,6)-tetra-O-pivaloyl-α/β-D-galactopyranoside-1-ol (Mbadugha, A. N. B. et al., *Org. Lett.* 2003, 5, 4041) (2.00 g, 5.74 mmol) in CH$_2$Cl$_2$ (10 mL). After 5 min, Cl$_3$CCN (1.2 mL, 11 mmol) was added drop-wise. The reaction was stirred at 0° C. for 2 h. Saturated aqueous NH$_4$Cl (50 mL) and the mixture was extracted with CH$_2$Cl$_2$ (3×30 mL). The combined organic layers were dried (MgSO$_4$), filtered and concentrated. The crude product was purified by flash column chromatography on silica gel (petroleum ether/EtOAc, 95:5) to give 4 (1.87 g, 53%) as a slightly yellowish viscous oil: $^1$H NMR (400 MHz, CDCl$_3$) δ 8.65 (br s, 1H), 6.60 (d, J=3.5 Hz, 1H), 5.56-5.54 (m, 1H), 5.52-5.11 (m, 1H), 5.40 (dd, J=10.6, 3.6 Hz, 1H), 4.47 (app ddd, J=6.5, 6.5 Hz, 1H), 4.08 (dd, J=11.4, 7.4 Hz, 1H), 4.03 (dd, J=11.3, 6.0 Hz, 1H), 1.25 (s, 9H), 1.13 (s, 9H), 1.12-1.11 (m, 18H). $^{13}$C NMR (100 MHz, CDCl$_3$) δ 178, 177.6, 177.4, 177.0, 160.9, 93.7, 91.1, 70.0, 67.9, 67.6, 67.1, 61.8, 39.3, 39.1, 39.0, 38.9, 27.4, 27.3, 27.3, 27.2, 27.2, 27.2; HRMS (TOP) m/z calculated (calcd) for C$_{28}$H$_{45}$Cl$_3$NO$_{10}$ [M$^+$+H] 659.2104, found [M-OCNHCCl$_3$] 499.2901.

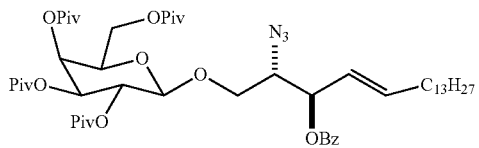

(2S,3R,4E)-2-Azido-3-benzoyloxy-1-(2,3,4,6-tetra-O-pivaloyl-β-galactopyranoside)octadec-4-ene (5)

(2,3,4,6-Tetra-O-pivaloyl-α-D-galactopyranoside)-1-trichloroacetimidate (4) (Zimmermann, P. et al., *J. Carbohydr. Chem.* 1988, 7, 435) (0.38 mg, 0.58 mmol) and (2S,3R,4E)-2-azido-3-benzoyloxyoctadec-4-en-1-ol (3) (0.21 g, 0.48 mmol) were dissolved in dry CH$_2$Cl$_2$ (7 mL), and the solution was stirred in the presence of 4 Å MS (300 mg) at room temperature (rt) for 30 min. BF$_3$·OEt$_2$ in dry CH$_2$Cl$_2$ (1.46 µL in 0.5 mL) was added within 10 min at 0° C. The reaction was slowly warmed to rt and stirred for 4 h. The reaction mixture was diluted with petroleum ether (15 mL) and then filtered. The filtrate was treated with saturated aqueous NaHCO$_3$ (5 mL). The organic layer was separated, and the aqueous phase was extracted with CH$_2$Cl$_2$ (3×5 mL). The combined organic layers were dried (MgSO$_4$), filtered and concentrated. Purification by COMBIFLASH column chromatography on silica gel (Acetone/hexane, 5:95) gave 5 (0.23 g, 51% β-product) as a colorless oil: (Zimmerman et al., ibid.) $^1$H NMR (400 MHz, CDCl$_3$) δ 8.03 (d, J=7.5 Hz, 2H), 7.54 (t, J=7.4, Hz, 1H), 7.42 (t, J=7.7, Hz 2H), 5.90 (dt, J=14.3, 6.8 Hz, 1H), 5.59-5.50 (m, 2H), 5.38 (d, J=1.3 Hz, 1H), 5.24 (dd, J=10.5, 8.1 Hz, 1H), 5.08 (dd, J=10.4, 3.1 Hz, 1H), 4.56 (d, J=7.9 Hz, 1H), 4.11 (dd, J=10.0, 5.7 Hz, 1H), 4.01-3.95 (m, 2H), 3.93-3.88 (m, 1H), 3.84 (dd, J=10.2, 7.2 Hz, 1H), 3.64 (dd, J=10.2, 4.8 Hz, 1H), 2.05 (dt, J=7.0, 7.0 Hz, 2H), 1.40-1.32 (m, 3H), 1.30-1.22 (m, 28H), 1.16 (s, 9H), 1.14 (s, 9H), 1.10 (s, 9H), 0.86 (t, J=7.0 Hz, 3H); $^{13}$C NMR (100 MHz, CDCl$_3$) δ 177.9, 177.4, 177.0, 176.6, 165.1, 138.4, 133.3, 130.1, 129.9, 128.6, 123.0, 101.1, 74.8, 71.3, 71.1, 68.6, 68.0, 66.8, 64.0, 61.2, 39.2, 38.9, 38.9, 38.8, 32.5, 32.1, 29.8, 29.7, 29.5, 29.5, 29.3, 28.6, 27.3, 27.2, 22.8, 14.3.

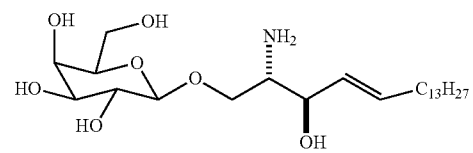

(2S,3R,4E)-2-Amino-1-(β-galactopyranosyloxy)octadec-4-en-3-ol (6)

NaOMe (0.5 M, 4 mL, 2.10 mmol) was added to a solution of (2S,3R,4E)-2-azido-3-benzoyloxy-1-(2,3,4,6- tetra-O-pivaloyl-β-galactopyranoside)octadec-4-ene (5) (0.32 g, 0.35 mmol) in a mixture of CH$_2$Cl$_2$/MeOH (2.8:2.8 mL). The reaction was stirred at rt for 1 h. The reaction was neutralized with Dowex (H$^+$ resin). The mixture was filtered through a pad of celite, and the celite was washed with mixture of CHCl$_3$/MeOH (1:1, 10 mL). The filtrate was concentrated and purified using flash column chromatography on silica gel (CH$_2$Cl$_2$/MeOH, 85:15) to give (2S,3R,4E)-2-azido-1-(galactopyranosyloxy)octadec-4-en-3-ol as a white solid (0.12 g, 69%): (Zimmerman et al., ibid.) $^1$H NMR (500 MHz, CDCl$_3$/CD$_3$OD, 3:2) δ 6.21 (dt, J=11.7, 6.6 Hz, 1H), 5.94 (dd, J=15.5, 7.3 Hz, 1H), 4.64-4.4 (m, 3H), 4.31 (s, 1H), 4.26-4.16 (m, 3H), 4.00 (dd, J=9.2, 9.2 Hz, 1H), 3.96-3.92 (m, 3H), 2.49 (dt, J=6.8, 6.8 Hz, 2H), 1.84-1.80 (m, 22H) 1.30 (t, J=7.0 Hz, 3H). $^{13}$C NMR (125 MHz, CDCl$_3$/CD$_3$OD=3:2) δ 1361, 129.0, 104.4, 76.0, 74.4, 72.9, 72.8, 72.1, 72.0, 69.9, 69.7, 69.6, 66.5, 62.3, 62.2, 33.3, 32.8, 30.5, 30.5, 30.5, 30.4, 30.3, 30.2, 30.1, 29.9, 23.5, 14.7. (2S,3R,4E)-2-Azido-1-(galactopyranosyloxy)octadec-4-en3-ol (90 mg, 0.20 mmol) in a mixture of pyridine/H$_2$O (1:1, 6 mL) was saturated with H$_2$S for 15 min. The reaction was stirred for 48 h. The solvent was evaporated, and the crude product was purified by flash column chromatography on silica gel (CH$_2$Cl$_2$/MeOH, 80:20) to give 6 (0.71 g, 80%) as yellowish brown crystals: (Zimmerman et al., ibid.) $[\alpha]^{25}_D$ −3.65 (c 1.0, (CHCl$_3$/MeOH, 3:2); IR 3356, 2920, 2851, 1466, 1053 cm$^{-1}$; $^1$H NMR (400 MHz, CDCl$_3$/CD$_3$OD, 3:2) δ 6.12 (dt, J=14.7, 6.7 Hz, 1H), 5.78 (dd, J=15.3, 7.3 Hz, 1H), 4.59 (d, J=7.4 Hz, 1H), 4.43 (dd, J=6.6, 6.6 Hz, 1H), 4.29 (dd, J=10.4, 7.2 Hz, 2H), 4.24 (app d, J=2.1 Hz, 1H), 4.19 (dd, J=11.8, 7.0 Hz, 1H), 4.12-4.07 (m, 2H), 3.72-3.70 (m, 1H), 2.41 (dt, J=6.6, 6.6 Hz, 2H), 1.80-1.61 (m, 22H), 0.84 (t, J=7.0 Hz, 3H). $^{13}$C NMR (100 MHz, CDCl$_3$/CD$_3$OD, 3:2) δ 135.9, 129.2, 104.0, 75.7, 74.0, 73.2, 71.8, 69.7, 62.3, 55.6, 33.0, 32.5, 30.3, 30.2, 30.1, 30.0, 29.8, 23.3, 14.6; HRMS (TOP) m/z calcd for C$_{24}$H$_{48}$NO$_7$ (M$^+$+H) 462.3425, found 462.3405.

15-Hexadecyn-1-ol (10)

1,3-Diaminopropane (13 mL) was added to a three neck round bottom flask charged with Li$^+$ wire (0.18 g, 25 mmol) under N$_2$. (Abrams, S. R. et al., *Org. Synthesis* 1988, 66, 127) The flask was fitted with a condenser. The mixture was stirred at rt for 30 min. A slight exothermic reaction resulted as the Li$^+$ dissolved, and a dark blue color was observed. The mixture was then stirred in a preheated oil bath at 70° C. until the blue color was discharged (approximately 1 h), affording a white suspension of lithium amide. This white color quickly changes to a magenta color. The reaction was cooled to rt, followed by addition of $^t$BuOK (2.10 g, 16.8 mmol). The resulting dark yellow/reddish brown solution was stirred for 20 min at rt, and then 9-hexadecyn-1-ol (9) (1.00 g, 4.19 mmol) was added via syringe drop-wise. The reaction was stirred for 1 h and then poured into ice H$_2$O (42 mL). The product was extracted with petroleum ether (3×20 mL). Extraction of product was difficult as it was cryalizing in the process; therefore Et$_2$O (3×50 mL) was used to finish the extraction. The combined organic layers were washed with H$_2$O (42 ml), 10% HCl (42 mL) and brine (42 mL). The organic layer was dried (MgSO$_4$), filtered and concentrated. The crude product was purified using flash column chromatography on silica gel (Petroleum ether/EtOAc, 90:10) to give 10 (697 mg, 70%) as a white crystalline solid: mp 48.0-49.0° C.; IR (neat) 3286, 2916, 2848, 1462, 1071, 720, 684, 627 cm$^{-1}$; $^1$H NMR (400 MHz, CDCl$_3$) δ 3.57 (t, J=6.7 Hz, 2H), 2.13 (dt, J=7.0, 2.6 Hz, 2H), 2.00 (s, 1H), 1.89 (t, J=2.6 Hz, 1H), 1.50 (m, 4H), 1.38-1.23 (m, 20H); $^{13}$C NMR (100 MHz, CDCl$_3$) δ 84.9, 68.2, 63.0, 32.9, 29.8, 29.7, 29.6, 29.6, 29.2, 28.9, 28.6, 25.9, 22.8, 18.5; HRMS (ESI) calcd for C$_{16}$H$_{31}$O [M+H]$^+$ m/z 239.2369, found 239.2374.

15,16-Tetracosadiyn-1-ol (11)

Cs$_2$CO$_3$ (4.22 g, 13.0 mmol), NaI (2.06 g, 13.7 mmol), and CuI (3.14 g, 16.4 mmol) were suspended in dry DMF (16 mL). After 5 min of stirring 15-hexadecyn-1-ol (10) (3.00 g, 12.6 mmol) in dry DMF (5 mL) was added, drop-wise and the solution stirred for 10 min. 1-bromo-2-octyne was added, and the reaction mixture was stirred for 24 h (monitored by $^1$H-NMR). (Tallman, K. A. et al., *J. Am. Chem. Soc.* 2009, 131, 5635) Saturated aqueous NH$_4$Cl (30 ml) was added, and the product was extracted with Et$_2$O (3×50 mL). The combined organic layers were washed with brine (3×15 mL), dried (MgSO$_4$), filtered and concentrated. The crude product was purified using flash column chromatography on silica gel (petroleum ether/Et$_2$O, 90:10), yielding 11 (1.60 g, 36%) as a yellowish solid. The product was light sensitive; therefore it was wrapped with aluminum foil and placed in the freezer immediately: mp 41.0-42.0° C.; IR (neat) 3286, 2917, 2849, 1462, 1071, 683, 628 cm$^{-1}$; $^1$H NMR (400 MHz, CDCl$_3$) δ 3.61 (t, J=6.6 Hz, 2H), 3.09 (dq, J=2.4, 2.4 Hz, 2H), 2.12 (tt, J=7.0, 2.2 Hz, 4H), 1.67 (br s, 1H), 1.54 (quin, J=6.7 Hz, 2H), 1.46-1.42 (m, 4H), 1.36-1.24 (m, 24H), 0.87 (t, J=7.0 Hz, 3H); $^{13}$C NMR (100 MHz, CDCl$_3$) δ 80.7, 74.7, 63.2, 33.0, 31.3, 29.8, 29.8, 29.7, 29.6, 29.3, 29.1, 28.9, 28.6, 25.9, 22.4, 18.9, 18.9, 14.1, 9.9; HRMS (ESI) calcd for C$_{24}$H$_{43}$O [M+H]$^+$ m/z 347.3308, found 347.3334.

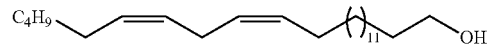

15Z,18Z-Tetracosadien-1-ol (12)

Pd/BaSO$_4$ (30.0 mg, 10% wt) and quinoline (0.1 mL) were added to a solution of 15,16-tetracosadiyn-1-ol (11) (0.50 g, 1.4 mmol) in hexane. (Tallman et al., ibid.) The reaction was purged for 10 min with H$_2$ and then stirred under H$_2$ for 3 h. The reaction was monitored by $^1$H-NMR. The reaction mixture was filtered through a pad of celite and the celite, was washed with hexane (20 mL). The filtrate was concentrated and purified using flash column chromatography on silica gel (Petroleum ether/Et$_2$O, 95:5) to give 12 with 17% of its inseparable E-isomer (0.27 g, 53%) as a colorless oil: IR (neat) 2917, 2849, 1462, 1071, 683 cm$^{-1}$; Peak assignments for 12: $^1$H NMR (400 MHz, CDCl$_3$) δ 5.41-5.30 (m, 4H), 3.64 (t, J=6.6 Hz, 2H), 2.77 (t, J=6.5 Hz, 2H), 1.57 (quin, J=7.3 Hz, 4H), 1.39-1.26 (m, 31H), 0.89 (t, J=6.6 Hz, 3H); $^{13}$C NMR (100 MHz, CDCl$_3$) δ 130.4, 128.2, 33.0, 31.8, 29.8, 29.8, 29.8, 29.7, 29.6, 29.6, 27.5, 27.4, 26.0, 25.9, 14.3; HRMS (ESI) calcd for C$_{24}$H$_{47}$O [M+H]$^+$ m/z 351.3621, found 351.3621.

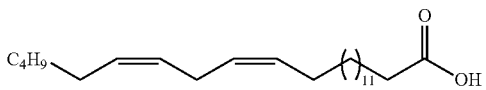

15Z,18Z-Tetracosadienoic acid (13)

Des Martin periodinane (0.16 g, 0.38 mmol) was added to a solution of 15Z,18Z-tetracosedien-1-ol (12) (0.12 g, 0.35 mmol) in dry CH$_2$Cl$_2$ (1.3 mL) at 0° C. The reaction was stirred at rt for 6 h. TLC still showed incomplete consumption of the alcohol, and the reaction was placed in the fridge overnight. The next day, the reaction mixture was filtered through a pad of celite, and the celite was washed with CH$_2$Cl$_2$ (10 mL). The combined filtrates were concentrated and purified by flash column chromatography on silica gel to provide 15Z,18Z-tetracosadienal as a colorless oil (53 mg, 43%, with E-isomer): IR (neat) 2920, 2850, 1700, 1650, 1510, 1100, 1050, 850 cm$^{-1}$; $^1$H NMR (400 MHz, CDCl$_3$) δ 9.76 (s, 1H), 5.41-5.30 (m, 4H), 2.77 (t, J=6.0 Hz, 2H), 2.41 (t, J=7.2 Hz, 2H), 2.04 (dt, J=6.3, 6.4 Hz, 4H), 1.61 (quin, J=6.7 Hz, 4H), 1.34-1.26 (m, 25H), 0.89 (t, J=6.9 Hz, 3H); $^{13}$C NMR (100 MHz, CDCl$_3$) δ 203.2, 130.4, 128.2, 44.1, 31.8, 29.9, 29.9, 29.8, 29.6, 29.6, 29.6, 27.4, 27.5, 27.4, 25.9, 22.8, 22.3, 14.3; HRMS (ESI) calcd for C$_{24}$H$_{45}$O [M+H]$^+$ m/z 349.3465, found 343.2579. NaHPO$_4$ (0.14 g, 1.0 mmol) was added to a mixture of 15Z,18Z-tetracosadienal (0.06 g, 0.18 mmol) and 2-methyl-2-butene (0.4 mL, 3.78 mmol) in $^t$BuOH (7 mL) and H$_2$O (1.5 mL) at 0° C. NaClO$_2$ (0.02 g, 0.22 mmol) was added in small portions and the mixture stirred for 6 h. One more equiv of NaClO$_2$ was added, and the reaction was left in the fridge overnight. The next day, TLC still showed remaining aldehyde; so another equivalent (equiv) of NaClO$_2$ was added, and the reaction mixture was stirred for 40 min at 0° C. After this, TLC showed complete consumption of the aldehyde. Saturated aqueous Na$_2$SO$_3$ and pH7 phosphate buffer (1:1, 2 mL) were added to quench the reaction. The product was extracted with EtOAc (3×10 mL). The combined organic layers were washed with sat. NH$_4$Cl (5 mL) and brine (5 mL), dried (MgSO$_4$), filtered and concentrated to give 13 (0.036 g, 51%) as a colorless oil: $^1$H NMR (400 MHz, CDCl$_3$) δ 5.41-5.30 (m, 4H), 2.77 (t, J=5.8 Hz, 2H), 2.34 (t, J=7.5 Hz, 2H), 2.05 (dt, J=7.0, 7.0 Hz, 4H), 1.63 (quin, J=7.2 Hz, 4H), 1.40-1.26 (m, 25H), 0.91-0.86 (m, 3H); $^{13}$C NMR (100 MHz, CDCl$_3$) δ 180.5, 130.4, 128.2, 34.3, 32.8, 31.8, 29.9, 29.8, 29.7, 29.6, 29.5, 29.3, 27.5, 27.4, 25.9, 22.8, 14.3.

Preparation of p-Nitrophenyl esters 7 p-Nitrophenol (1.1 equiv) and DMAP 0.2 equiv.) were added to a flask charged with carboxylic acid (1.0 equiv.) in dry CH$_2$Cl$_2$ (0.014 M) and stirred for 15 min. DCC (1.04 equiv) in dry CH$_2$Cl$_2$ (0.12 M) was then added slowly. The solution was allowed to stir at rt overnight. The reaction was filtered through a pad of celite and the celite was washed with more CH$_2$Cl$_2$. The combined filtrates were then concentrated. Purification via flash chromatography on silica gel (petroleum ether/EtOAc, 95:5) yielded PNP-activated esters.

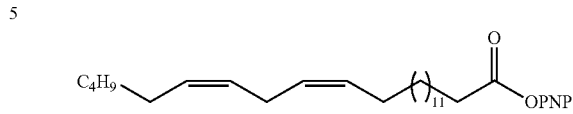

p-Nitrophenyl 15Z,18Z-tetracosedienoate (7a)

Compound 7a was afforded as a colorless solid/oil (29.0 mg, 73%): IR (neat) 2922, 2852, 1768, 1593, 1524, 1490, 1464, 1345, 1208, 1098, 863 cm$^{-1}$; $^1$H NMR (400 MHz, CDCl$_3$) δ 8.18 (d, J=9.0 Hz, 2H), 7.19 (d, J=8.9 Hz, 2H), 5.33-5.21 (m, 4H), 2.71-2.64 (m, 2H), 2.52 (t, J=7.4 Hz, 2H), 1.97 (dt, J=6.2, 6.2 Hz, 5H), 1.68 (quin, J=7.2 Hz, 2H), 1.36-1.20 (m, 26H), 0.81 (t, J=6.1 Hz, 3H); $^{13}$C NMR (100 MHz, CDCl$_3$) δ 171.4, 155.7, 145.4, 130.3, 128.1, 125.3, 122.6, 34.5, 31.7, 29.8, 29.8, 29.6, 29.5, 29.4, 29.2, 27.6, 27.4, 25.8, 24.9, 22.8, 14.2; HRMS (ESI) calcd for C$_{30}$H$_{48}$NO$_4$ [M+H]$^+$ m/z 486.3578, found 486.3570.

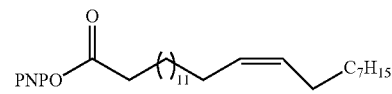

p-Nitrophenyl 15Z-tetracosenoate (7b)

Compound 7b was isolated as a colorless solid (0.50 g, 73%): mp 35.5-36.0° C.; IR (neat) 2916, 2850, 1753, 1593, 1536, 1490, 1471, 1350, 1203, 1138, 926, 868, 717 cm$^{-1}$; $^1$H NMR (400 MHz, CDCl$_3$) δ 8.18 (d, J=8.7 Hz, 2H), 7.19 (d, J=8.6 Hz, 2H), 5.27 (dt, J=15.3, 11.6 Hz, 2H), 2.51 (t, J=7.3 Hz, 2H), 1.96-1.91 (m, 4H), 1.68 (quin, J=7.0 Hz, 2H), 1.34-1.19 (m, 32H), 0.80 (t, J=6.7 Hz, 3H); $^{13}$C NMR (100 MHz, CDCl$_3$) δ 171.4, 155.7, 145.4, 130.1, 130.0, 125.3, 122.6, 34.5, 32.1, 30.0, 29.8, 29.8, 29.7, 29.6, 29.5, 29.4, 29.2, 27.4, 24.9, 22.9, 14.3; HRMS (ESI) calcd for C$_{30}$H$_{50}$NO$_4$ [M+H]$^+$ m/z 488.3734, found 488.3755.

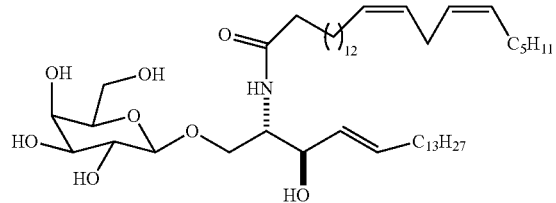

(2S,3R,4E)-1-(β-D-Galactopyranosyloxy)-2-(N-15Z, 18Z-tetracosadienoylamino)octadec-4-en-3-ol (8)

p-Nitrophenyl 15Z,18Z-tetracosadieneoate (7a) (28 mg, 0.060 mmol) was added to a solution of (2S,3R,4E)-2-amino-1-(β-galactopyranosyloxy)octadec-4-en-3-ol (6) (25 mg, 0.60 mmol) in pyridine (1 mL). The mixture was stirred in a preheated oil bath at 40° C. overnight. The reaction was concentrated and purified by flash column chromatography on silica gel (CH$_2$Cl$_2$/MeOH, 90:10) to give 8 (21 mg, 46%)

as an off white solid: mp 129.0-130.0° C.; [α]$^{25}_D$ −0.68 (c 1.83, CH$_2$Cl$_2$/MeOH, 3:2); IR (neat) 3302, 2915, 1641, 1544, 1467, 1082, 718 cm$^{-1}$; $^1$H NMR (400 MHz, CDCl$_3$/ CD$_3$OD, 3:2) δ 5.70 (dt, J=14.6, 6.6 Hz, 1H), 5.46 (dd, J=15.3, 7.2 Hz, 1H), 5.41-5.29 (m, 4H), 4.21 (d, J=7.4 Hz, 1H), 4.00 (ddd, J=7.3, 3.7, 3.7 Hz, 1H), 3.82 (app dd, J=2.6 Hz, 1H), 3.81 (dd, J=11.5, 6.6 Hz, 1H), 3.75 (dd, J=11.5, 5.0 Hz 1H), 3.62 (dd, J=10.3, 3.2 Hz, 1H), 3.57-3.47 (m, 3H), 2.77 (t, J=6.2 Hz, 2H), 2.17 (t, J=7.4 Hz, 2H), 2.07-1.99 (m, 6H), 1.59 (quin, J=7.1 Hz, 2H), 1.40-1.27 (m, 55H), 0.88 (t, J=6.9 Hz, 6H); $^{13}$C NMR (100 MHz, CDCl$_3$/CD$_3$OD, 3:2) δ 175.6, 135.0, 131.0, 130.3, 128.9, 104.8, 76.1, 74.5, 73.1, 72.4, 70.0, 69.7, 62.5, 54.5, 37.4, 33.2, 32.8, 32.4, 30.5, 30.5, 30.4, 30.3, 30.3, 30.2, 28.1, 28.1, 26.8, 26.5, 23.5, 23.4, 14.7; HRMS (ESI) calcd for C$_{48}$H$_{90}$NO$_8$ [M+H]$^+$ m/z 808.6661, found 808.6660.

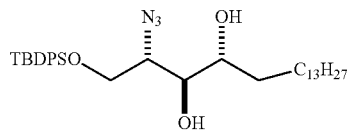

(2S,3S,4R)-2-Azido-1-(tert-butyldiphenylsilyloxy)
octadecan-3,4-diol (14)

NaN$_3$ (20.5 g, 31.5 mmol) was dissolved in a mixture of H$_2$O (50 mL) and CH$_2$Cl$_2$ (85 mL) and cooled to 5° C. Tf$_2$O (10.5 mL, 63.0 mmol) was slowly added via syringe over 15 min. The resulting mixture was vigorously stirred in an ice bath for 2 h. The in situ generated Tf$_2$N$_3$ in the CH$_2$Cl$_2$ was separated and the aqueous phase was then extracted with CH$_2$Cl$_2$ (2×24 mL). The combined organic layers were washed with saturated aqueous Na$_2$CO$_3$ (100 mL). This solution was added to a suspension of ribo-phytosphingosine (10.0 g 31.5 mmol), K$_2$CO$_3$ (6.53 g, 47.3 mmol) and Cu$_2$SO$_4$ (79.0 mg, 0.32 mmol) in a mixture of H$_2$O (100 mL) and MeOH (200 mL) at 0° C. The solution was allowed to stir at rt overnight. The next day, the solvents were evaporated. H$_2$O (300 mL) was added to the solid residue and resulting mixture was allowed to stir for 2 h. The product was extracted with EtOAc (3×200 mL). The combined organic layers were filtered through celite, and the filtrate was concentrated to yield (2S,3S,4R)-2-azidooctadecan-1, 3,4-triol (14.6 g, crude) as a bluish solid. (Trappeniers, M. et al., Chem. Med. Chem. 2008, 3, 1061) This product was carried forward to the next step without purification.

TBDPSCl (13 mL, 51 mmol) was added drop-wise to 2S,3S,4R)-2-azidooctadecan-1,3,4-triol (14.6 g, 42.6 mmol) and DMAP (0.26 g, 2.1 mmol) mixture in dry pyridine (47 mL) and CH$_2$Cl$_2$ (200 mL). The mixture was stirred for 48 h. The reaction was diluted with EtOAc (200 ml) and washed with brine (200 mL), dried (MgSO$_4$), filtered and concentrated under reduced pressure. The crude product was purified using flash column chromatography on silica gel (petroleum ether/EtOAc, 90:10) to provide 14 as slightly yellow oil (17.0 g, 70%): (Veerapen, N. et al., Bioorg. Med. Chem. Lett. 2009, 19, 4288) [α]$^{25}_D$ 16.9 (c 1.13, CDCl$_3$); IR (neat) 2923, 2853, 2097, 1428, 1111, 823, 738, 700, 503 cm$^{-1}$; $^1$H NMR (400 MHz, CDCl$_3$) δ 7.70 (d, J=7.2 Hz, 4H), 7.48-7.39 (m, 6H), 4.04 (dd, J=11.0, 4.2 Hz, 1H), 3.92 (dd, J=10.9, 5.7 Hz, 1H), 3.69 (s, 2H), 3.37 (ddd, J=5.4, 5.4, 5.4 Hz, 1H), 2.49 (d, J=3.1 Hz, 1H), 1.97 (s, 1H), 1.60-1.39 (m, 4H), 1.35-1.26 (m, 20H), 1.09 (s, 9H), 0.88 (t, J=7.0, 3H); $^{13}$C NMR (100 MHz, CDCl$_3$) δ 135.9, 135.8, 132.8, 132.7, 130.3, 128.1, 74.4, 72.6, 64.4, 63.6, 32.1, 32.1, 29.9, 29.9, 29.8, 29.8, 29.6, 27.0, 25.9, 22.9, 19.3, 14.3; HRMS (ESI) calcd for C$_{34}$H$_{56}$N$_3$O$_3$Si [M+H]$^+$ m/z 582.4085, found 582.4119.

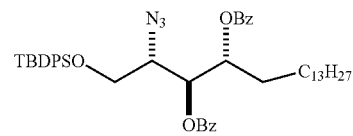

(2S,3S,4R)-2-Azido-(3,4-dibenzoyloxy-1-tert-butyl-
diphenylsilyloxy)octadecane (15)

BzCl (6.10 mL, 52.8 mmol) was added to a solution of (2S,3S,4R)-2-azido-1-(tert-butyldiphenylsilyloxy)octadecane-3,4-diol (14) (5.00 g, 8.80 mmol) and DMAP (0.19 g, 1.6 mmol) in pyridine (78 mL). The reaction mixture was allowed to stir overnight. Ice-cold H$_2$O (120 mL) was added to the reaction to quench it. The solution was extracted with CH$_2$Cl$_2$ (3×100 mL). The combined organic layers were dried (MgSO$_4$), filtered and concentrated. Flash chromatography purification of the crude product on silica gel (petroleum ether/EtOAc, 95:5) gave 15 (5.43 g, 80%) as a colorless oil: (Veerapen, N. et al., Bioorg. Med. Chem. Lett. 2009, 19, 4288) [α]$^{25}_D$ 6.21 (c 1.28, CH$_2$Cl$_2$); IR (neat) 2923, 2853, 2099, 1724, 1451, 1260, 1104, 1068, 707, 503 cm$^{-1}$; $^1$H NMR (400 MHz, CDCl$_3$) δ 7.83 (d, J=7.2 Hz, 2H), 7.79 (d, J=7.2 Hz, 2H), 7.56 (dd, J=7.8, 1.2 Hz, 2H), 7.49 (d, J=7.3 Hz, 3H), 7.46-7.42 (m, 1H), 7.33-7.22 (m, 8H), 7.14 (t, J=7.3 Hz, 2H), 5.46-5.41 (m, 2H), 3.93-3.87 (m, 1H), 3.81-3.75 (m, 2H), 1.72 (dt, J=9.1, 9.1 Hz, 2H), 1.35-1.14 (m, 24H), 0.96 (s, 9H), 0.79 (t, J=7.0 Hz, 3H); $^{13}$C NMR (100 MHz, CDCl$_3$) δ 165.8, 165.2, 135.7, 135.7, 133.5, 133.2, 132.9, 132.6, 130.1, 130.0, 130.0, 129.9, 129.7, 128.7, 128.6, 128.0, 127.9, 73.3, 72.4, 64.3, 63.4, 32.1, 30.0, 29.8, 29.8, 29.7, 29.6, 29.6, 26.8, 25.6, 22.9, 19.2, 14.3; HRMS (ESI) calcd for C$_{48}$H$_{64}$N$_3$O$_5$Si m/z 790.4610, found 790.4652.

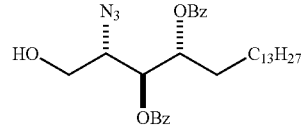

(2S,3S,4R)-2-Azido-(3,4-dibenzoyloxy)octadecan-1-
ol (16)

AcCl (9.10 mL) was added drop-wise to MeOH (230 mL). (2S,3S,4R)-2-azido-(3,4-dibenzoyloxy-1-tert-butyldiphenylsilyloxy)octadecane (15) (5.43 g, 6.99 mmol) in Et$_2$O (230 mL) was the added drop-wise. (Nashed et al., ibid.) The solution was stirred for 2 d. Saturated aqueous NaHCO$_3$ was added to neutralize the reaction to pH 7. The two layers were separated, and the aqueous layer was extracted with CH$_2$Cl$_2$ (3×100 mL). The combined organic layers were dried (MgSO$_4$), filtered and concentrated. The crude product was purified by flash column chromatography on silica gel (petroleum ether/EtOAc 90:10) to give 16 (2.14 g, 69%) as a colorless solid (Veerapen et al., ibid.) mp 54.0-55.0° C.; [α]$^{25}_D$ 17.3 (c 1.05, CHCl$_3$); IR (neat) 2918, 2107, 1712, 1246, 1109, 1026, 706, 685 cm$^{-1}$; $^1$H NMR (400 MHz, CDCl$_3$) δ 8.05 (d, J=7.3 Hz, 2H), 8.01 (d, J=7.3 Hz, 2H), 7.59 (t, J=7.4 Hz, 1H), 7.53 (t, J=7.5 Hz, 1H), 7.44 (t, J=7.8 Hz, 2H), 7.40 (t, J=7.8 Hz, 2H), 5.61-5.56 (m, 2H), 4.03-4.00 (m, 1H), 3.88-3.79 (m, 2H), 3.11 (s, 1H), 2.02-1.87 (m, 2H), 1.57-1.38 (m, 2H), 1.40-1.26 (m, 22H), 0.88 (t, J=7.0 Hz, 3H); $^{13}$C NMR (100 MHz, CDCl$_3$) δ 166.1, 165.7, 133.7, 133.3, 129.9, 129.8, 129.3, 128.7, 128.5, 73.4, 73.0, 63.3, 62.2, 32.0, 29.7, 29.7, 29.7, 29.5, 29.5, 29.4, 25.5, 22.8, 14.2; HRMS (ESI) calcd for C$_{32}$H$_{46}$N$_3$O$_5$ [M+H]$^+$ m/z 552.3432, found 552.3433.

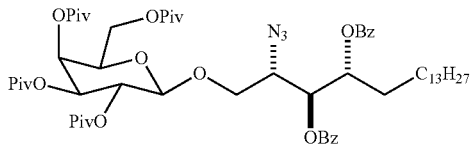

(2S,3S,4R)-2-Azido-3,4-dibenzoyloxy-1-(2,3,4,6-tetra-O-pivaloyl-β-galactopyranoside)octadecane (17)

(2,3,4,6-Tetra-O-pivaloyl-α-D-galactopyranoside)-1-trichloro-acetimidate (4) (0.60 mg, 0.99 mmol) and (2S,3S,4R)-2-azido-(3,4-dibenzoyloxy)octadecan-1-ol (16) (0.45 g, 0.82 mmol) were dissolved in dry CH$_2$Cl$_2$ (13 mL), and the solution was stirred in the presence of 4 Å MS (600 mg) at rt for 10 min. BF$_3$·OEt$_2$ in dry CH$_2$Cl$_2$ (1.46 μL in 2 mL) was added within 10 min at −10° C. and the reaction was slowly warmed to rt and stirred for 1.5 h.$^5$ The reaction mixture was diluted with petroleum ether (50 mL) and then filtered. The filtrate was treated with saturated aqueous NaHCO$_3$ (10 mL). The organic layer was separated and the aqueous phase was extracted with CH$_2$Cl$_2$ (3×15 mL). The combined organic layers were dried (MgSO$_4$), filtered and concentration. Purification by flash column chromatography on silica gel (petroleum ether/EtOAc 95:5) gave 17 (0.34 g, 39%, β-product) as a colorless oil: [α]$^{25}_D$ −3.65 (c 1.00, CH$_2$Cl$_2$); IR (neat) 2926, 2103, 1728, 1480, 1261, 1140, 710 cm$^{-1}$; $^1$H NMR (500 MHz, CDCl$_3$) δ 8.00 (d, J=7.8 Hz, 4H), 7.57 (dt, J=12.0, 7.4 Hz, 2H), 7.44 (t, J=15.6, 7.8 Hz, 4H), 5.49-5.44 (m, 2H), 5.37 (d, J=3.1 Hz, 1H), 5.22 (d, J=10.5, 8.1 Hz, 1H), 5.05 (dd, J=10.4, 3.2 Hz, 1H), 4.56 (d, 0.1=7.9 Hz, 1H), 4.08-4.02 (m, 2H), 3.98-3.90 (m, 4H), 1.88-1.80 (m, 2H), 1.43-1.32 (m, 3H), 1.29-1.20 (m, 30H), 1.14 (s, 9H), 1.09 (s, 9H), 1.08 (s, 9H), 0.86 (t, J=6.7 Hz, 3H). $^{13}$C NMR (125 MHz, CDCl$_3$) δ 177.9, 177.4, 177.0, 176.5, 133.7, 133.4, 130.0, 129.9, 129.8, 129.5, 128.7, 128.6, 100.9, 73.0, 71.2, 71.1, 68.7, 68.6, 66.7, 61.4, 61.1, 38.9, 38.9, 38.8, 32.0, 30.3, 29.8, 29.8, 29.8, 29.8, 29.8, 29.7, 29.7, 29.6, 29.5, 29.5, 29.5, 25.4, 22.8, 14.2; HRMS (ESI) calcd for C$_{58}$H$_{88}$N$_3$O$_{14}$[M+H]$^+$ m/z 1050.6261, found 1050.6300.

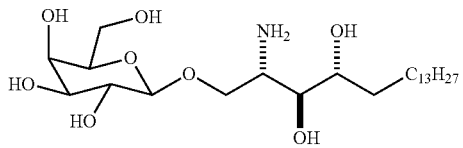

(2S,3S,4R)-2-Amino-1-(β-galactopyranosyloxy)octadecan-3,4-diol (18)

NaOMe (3.9 mL, 1.97 mmol) was added to a solution of (2S,3S,4R)-2-azido-3,4-dibenzoyloxy-1-(tetra-O-pivaloyl-β-galactopyranoside)octadecane (17) (296 mg, 0.28 mmol) in a mixture of CH$_2$Cl$_2$/MeOH (3.4/3.4 mL). (Zimmerman, P. et al., ibid.) The solution was stirred at rt for 1.5 h. The reaction was acidified to pH 2 with dowex (H$^+$ resin). The mixture was filtered through a pad of celite, and the celite was washed with 1:1 mixture of CHCl$_3$ and MeOH (15 mL). The filtrate was concentrated and triturated with petroleum ether/EtOAc (85:15) to give (2S,3S,4R)-2-azido-1-(β-galactopyranosyloxy)octadecan-3,4-diol (134 mg, 94%) as a white solid: [α]$^{25}_D$ 18.88 (c 6.643, CHCl$_3$/MeOH, 3:2); IR (neat) 3355 (br), 2915, 2849, 2096, 1255, 1071, 719 cm$^{-1}$; $^1$H NMR (400 MHz, CDCl$_3$/CD$_3$OD, 3:2) δ 4.28 (d, J=7.2 Hz, 1H), 4.13 (dd, J=10.6, 5.0 Hz, 1H), 3.96 (d, J=10.3 Hz, 1H), 3.97 (s, 1H), 3.82 (dd, J=11.5, 6.5 Hz, 1H), 3.70-3.63 (m, 4H), 3.58-3.49 (m, 3H), 1.67-1.56 (m, 2H), 1.42-1.25 (m, 24H), 0.87 (t, J=6.8 Hz, 3H). $^{13}$C NMR (100 MHz, CDCl$_3$/CD$_3$OD, 3:2) δ 104.3, 76.1, 74.9, 74.4, 72.7, 72.1, 69.9, 69.4, 63.1, 62.3, 33.2, 32.8, 30.6, 30.5, 30.5, 30.2, 26.6, 23.5, 14.7; HRMS (ESI) calcd for C$_{74}$H$_{48}$N$_3$O$_8$ [M+H]$^+$ m/z 506.3436, found 506.3511.

The product was carried forward to reduction. (2S,3S,4R)-2-azido-1-(β-galactopyranosyloxy)octadecan-3,4-diol (13 mg, 0.27 mmol) in a mixture of pyridine/H$_2$O (1:1, 7.6 mL) was saturated with H$_2$S. The reaction was stirred for 48 h. (Zimmerman, P. et al., ibid.) The solvent was evaporated to give 18 (136 mg, crude) as a yellowish brown powder, which was carried forward without purification.

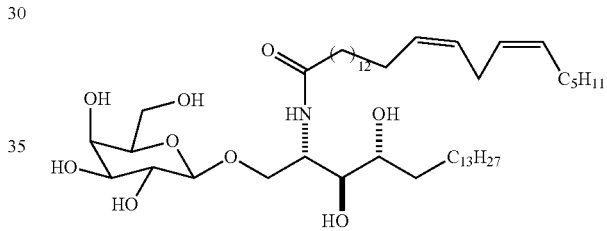

2S,3S,4E)-1-(β-D-Galactopyranosyloxy)-2-(N-15Z,18Z-tetracosadienoyl-amino)octadecan-3.4-diol (19a).

p-Nitrophenyl 15Z,18Z-tetracosadieneoate (7a) (28 mg, 0.06 mmol) was added to a solution of (2S,3S,4R)-2-amino-1-(β-galactopyranosyloxy)octadecan-3,4-diol (18) (27.0 mg, 0.06 mmol) in pyridine (1 mL). The mixture was stirred in a preheated oil bath at 40° C. overnight. The reaction was concentrated and purified by flash column chromatography on silica gel (CH$_2$Cl$_2$/MeOH, 95:5) to give 19a (19 mg, 40%) as a white solid: mp 169.0-171.0° C.; [α]$^{25}_D$ 8.81 (c 1.86, CHCl$_3$/MeOH, 3:2); IR (neat) 3302, 2918, 2850, 1637, 1467, 1082, 721 cm$^{-1}$; 1H NMR (400 MHz, CDCl$_3$/CD$_3$OD, 3:2) δ 5.41-5.29 (m, 4H), 4.23-4.22 (m, 2H), 4.14-4.12 (m, 1H), 3.87 (app dd, J=2.0 Hz, 1H), 3.82 (dd, J=11.6, 6.8 Hz, 1H), 3.72 (ddd, J=13.4, 13.4, 4.7 Hz, 2H), 3.61-3.47 (m, 5H), 2.77 (t, J=6.1 Hz, 2H), 2.20 (t, J=7.4 Hz, 2H), 2.05 (dt, J=6.4, 6.4 Hz, 2H), 2.04-2.00 (m, 2H), 1.68-1.51 (m, 5H), 1.44-1.27 (m, 49H), 0.88 (t, J=4.8 Hz, 6H); $^{13}$C NMR (100 MHz, CDCl$_3$ CDCl$_3$/CD$_3$OD, 3:2) δ 175.6, 131.0, 128.9, 76.3, 75.5, 74.5, 73.3, 72.4, 70.1, 70.1, 62.6, 51.5, 37.4, 33.2, 32.8, 32.4, 30.7, 30.6, 30.4, 30.3, 30.3, 30.2, 28.1, 28.1, 26.8, 26.8, 26.5, 23.5, 23.4, 14.7; HRMS (TOF) m/z calcd for C$_{48}$H$_{92}$NO$_9$ [M−H]$^+$ 826.6767, found 826.6777.

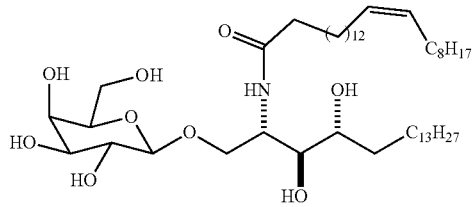

(2S,3S,4R)-1-(β-D-Galactopyranosyloxy)-2-(N-15Z-tetracosenoylamino)octa-decan-3,4-diol (19b)

p-Nitrophenyl 15Z-tetracosenoate (7b) (33 mg, 0.07 mmol) was added to a solution of (2S,3S,4R)-2-amino-1-(β-galactopyranosyloxy)octadecan-3,4-diol (60) (30 mg, 0.06 mmol) in pyridine (1 mL). The mixture was stirred in a preheated oil bath at 40° C. overnight. The reaction was concentrated and purified by flash column chromatography on silica gel (CH$_2$Cl$_2$/MeOH, 95:5) to give 19b (19 mg, 38%) as a white solid: mp 169.0-171.0° C.; $[\alpha]^{25}_D$ 7.38 (c 0.82, CHCl$_3$/MeOH, 3:2); IR (neat) 3330, 2917, 2849, 1637, 1545, 1465, 1081, 1049, 721 cm$^{-1}$; $^1$H NMR (400 MHz, CDCl$_3$/CD$_3$OD, 3:2) δ 5.38-5.30 (m, 2H), 4.24-4.20 (m, 2H), 4.16 (dd, J=10.3, 4.6 Hz, 1H), 3.87 (app dd, J=2.7 Hz, 1H), 3.82 (dd, J=11.6, 6.8 Hz, 1H), 3.72 (ddd, J=11.1, 11.1, 4.8 Hz, 2H), 3.61-3.47 (m, 5H), 2.20 (t, J=7.6 Hz, 2H), 2.01 (dt, J=6.8, 6.8 Hz, 2H), 2.04-2.00 (m, 2H), 1.68-1.57 (m, 3H), 1.53-1.51 (m, 1H), 1.47-1.27 (m, 56H), 0.88 (t, J=6.0 Hz, 6H); $^{13}$C NMR (100 MHz, CDCl$_3$/CD$_3$OD, 3:2) δ 175.5, 130.7, 104.8, 76.2, 75.5, 74.5, 73.3, 72.4, 70.1, 70.1, 51.5, 37.4, 33.6, 32.7, 30.6, 30.6, 30.5, 30.4, 30.3, 30.3, 30.2, 30.1, 28.0, 26.8, 26.7, 23.5, 14.6; HRMS (TOF) m/z calcd for C$_{48}$H$_{94}$NO$_9$ [M−H]$^+$ 828.6923, found 828.6915.

General Sulfation Procedure

Glycolipids (1 equiv) and Bu$_2$SnO (1.2 equiv) were refluxed in MeOH (0.016 M) for 2 h. The solvent was evaporated under reduced pressure. The resulting dibutylstannylene complex was treated with Me$_3$N·SO$_3$ (2 equiv) in THF (2 mL). (Guilbert, B. et al., *Tetrahedron Asymmetry* 1994, 5, 2163; Compostella, F. et al., *Tetrahedron* 2002, 58, 8703) The mixture was stirred at rt from between 2 to 6 h. TLC was used to monitor the reaction. The solvent was evaporated, and the residue dissolved in a 1:1 mixture of CH$_3$Cl$_3$/MeOH (4 mL). Dowex (Na$^+$ resin) was added. The mixture was then stirred for 10 min, followed by filtration and concentration. The crude product was partitioned in a mixture of 1-butanol/H$_2$O (1:1, v/v) and centrifuged. The supernatants (1-butanol, containing the sulfatides) was collected and concentrated. Purification by flash column chromatography on silica gel (CH$_2$Cl$_2$/MeOH, 10 to 15%1 gave the sulfatides.

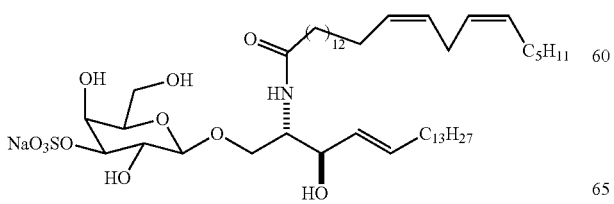

(2S,3R,4E)-1-(3-O-Sodiumsulfonyl-β-D-galactopyranosyloxy)-2-(N-15Z,18Z-tetracosadienoylamino)octadec-4-en-3-ol (C24:1).

Sulfatide C24:1 was isolated as an off white solid (14.9 mg, 65%): mp 182.0-183.0° C.; $[\alpha]^{25}$D 8.28 (c 0.72, CHCl$_3$/MeOH, 3:2); IR (neat) 3370 (br), 2918, 2850, 1644, 1467, 1258, 1066 cm$^{-1}$; $^1$H NMR (400 MHz, CDCl$_3$/CD$_3$OD, 3:2) δ 5.70 (dt, J=15.3, 6.6 Hz, 1H), 5.44 (dd, J=15.4, 7.4 Hz, 1H), 5.40-5.29 (m, 4H), 4.34 (d, J=7.7 Hz, 1H), 3.64 (dd, J=10.3, 3.2 Hz, 1H), 3.57 (dd, J=5.7, 5.7 Hz, 1H), 2.77 (dd, J=6.3, 6.3 Hz, 4H), 2.17 (t, J=7.6 Hz, 2H), 2.08-2.00 (m, 7H), 1.65-1.51 (m, 2H), 1.40-1.27 (m, 48H), 0.91-0.86 (m, 6H); $^{13}$C NMR (100 MHz, CHCl$_3$/CD$_3$OD, 3:2) δ 175.8, 135.2, 131.1, 130.4, 128.9, 104.5, 81.4, 75.8, 72.9, 70.6, 69.9, 68.6, 62.4, 54.5, 37.4, 33.2, 32.8, 32.4, 30.6, 30.5, 30.5, 30.4, 30.4, 30.3, 30.2, 28.1, 28.1, 26.9, 26.6, 23.5, 23.4, 14.7; HRMS (TOF) m/z calcd for C$_{46}$H$_{86}$NO$_{11}$S [M−Na]$^+$ 860.5922, found 860.5923.

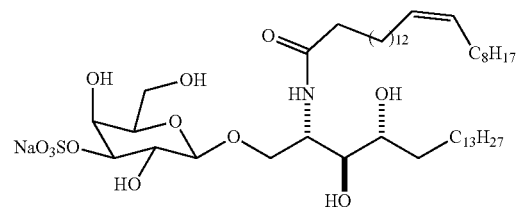

(2S,3S,4R)-1-(3-O-Sodiumsulfonyl-β-D-galactopyranosyloxy)-2-(N-15Z-tetracosenoylamino)octadecane-3,4-diol (pC24:1)

Sulfatide pC24:1 was isolated as a white solid (5.3 mg, 58%): mp 211.4-212.4° C.; $[\alpha]^{25}_D$ 8.33 (c 0.50, CHCl$_3$/MeOH, 3:2); IR (neat) 3367 (br), 2917, 2850, 1643, 1466, 1224, 1066, 812 cm$^{-1}$; $^1$H NMR (400 MHz, CDCl$_3$/CD$_3$OD, 3:2) δ 5.37-5.30 (m, 2H), 4.34 (d, J=7.7 Hz, 1H), 3.81 (dd, J=4.9, 3.1 Hz, 1H), 3.76-3.56 (m, 2H), 3.70-3.64 (m, 2H), 3.59-3.57 (m, 2H), 2.20 (t, J=7.6 Hz, 2H), 2.04-2.00 (m, 4H), 1.64-1.50 (m, 4H), 1.44-1.26 (m, 56H), 0.87 (t, J=6.4 Hz, 6H); $^{13}$C NMR (100 MHz, CDCl$_3$/CD$_3$OD) δ 175.8, 130.8, 104.2, 81.3, 75.8, 74.9, 73.2, 70.5, 70.1, 68.3, 62.3, 51.2, 37.4, 37.3, 32.9, 32.8, 30.7, 30.7, 30.6, 30.6, 30.5, 30.4, 30.4, 30.3, 30.2, 30.2, 28.1, 27.0, 26.9, 23.6, 14.8; HRMS (TOF) m/z calcd for C$_{48}$H$_{90}$NO$_{12}$S [M−Na]$^+$ 906.6340, found 906.6339.

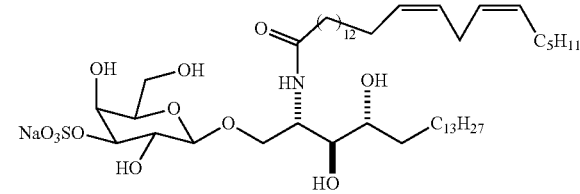

(2S,3S,4R)-1-(3-O-Sodiumsulfonyl-β-D-galactopyranosyloxy)-2-(N-15Z,18Z-tetracosadienoylamino)octadecan-3,4-diol (pC24:2).

Sulfatide pC24.2 was isolated as an off white solid (8.0 mg, 48%): mp 172.0-173.0° C.; $[\alpha]^{25}_D$ 11.15 (c 0.49, CHCl$_3$/MeOH, 3:2); IR (neat) 3400 (br), 2917, 2850, 1637, 1467, 1226, 1061 cm$^{-1}$; $^1$H NMR (500 MHz, CDCl$_3$/CD$_3$OD, 3:2) δ 5.41-5.30 (m, 4H), 3.81-3.78 (m, 1H), 3.75-3.72 (m, 2H), 3.69-3.64 (m, 211), 3.60-3.57 (m, 2H), 2.77 (t, J=6.6 Hz, 1H), 2.20 (t, J=7.3 Hz, 2H), 2.07-2.02 (m, 4H), 1.59-1.52 (m, 4H), 1.38-1.26 (m, 49H), 0.88 (m, 6H); $^{13}$C NMR (125 MHz, CDCl$_3$/CD$_3$OD, 3:2) δ 175.8, 131.1, 131.0, 128.9, 128.9, 104.2, 81.3, 75.8, 74.8, 73.3, 70.5, 70.1, 68.3, 62.3, 54.4, 37.3, 37.3, 32.8, 32.6, 32.4, 30.6, 30.5, 30.4, 30.3, 30.2, 28.1, 28.1, 26.9, 26.8, 26.5, 23.5, 23.4, 14.8; HRMS (TOF) calcd for C$_{48}$H$_{92}$NO$_{12}$S$^-$ [M−Na]$^+$ m/z 904.6189, found 904.6210.

Example 6

This example demonstrates that 5 nmol C24:2 efficiently reduces tumor nodules in mice.

WT BALB/c mice were inoculated i.v. with 5×10$^5$ CT26 cells and treated i.p. with 30, 5 or 0.5 nmol of sulfatide or C24:2. The number of nodules in the lung was determined 8 to 12 days after injection. The results are shown in FIG. 6. As shown in FIG. 6, C24:2 is efficient for the reduction of tumor nodules at the dose of 5 nmol.

Example 7

This example demonstrates that C24:2 induced a high production of IFN-γ in the serum of mice.

Mice were injected i.p. with lipids and bled 3, 6, 12 and 24 h after injection. The cytokine production in the serum was determined by multiplex analysis. The results are shown in FIG. 7. As shown in FIG. 7, C24:2 injection induced a high production of IFN-γ in the serum.

Example 8

This example demonstrates that the C24:2-induced protection from tumor nodules is dependent on IFN-γ.

WT BALB/c mice were injected i.v. with 0.5×10$^6$ CT26 (colon cancer cells) and treated the same day with 30 μmol of sulfatide or C24:2 or 500 pmol of α-GalCer injected i.p. Mice were injected i.p with 200 μg/ml of anti-IFNγ or rat IgG isotype control on day 0, day 1, day 2, day 3, and day 5. Lung nodules were counted 8 to 12 days after tumor inoculation according to the results in the monitoring mice. The results are shown in FIG. 8A (Rat IgG) and FIG. 8B (anti-IFN-γ). As shown in FIGS. 8A-8B, the C24:2-induced protection from tumor nodules is dependent on IFN-γ.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula (Ic) or (IIc):

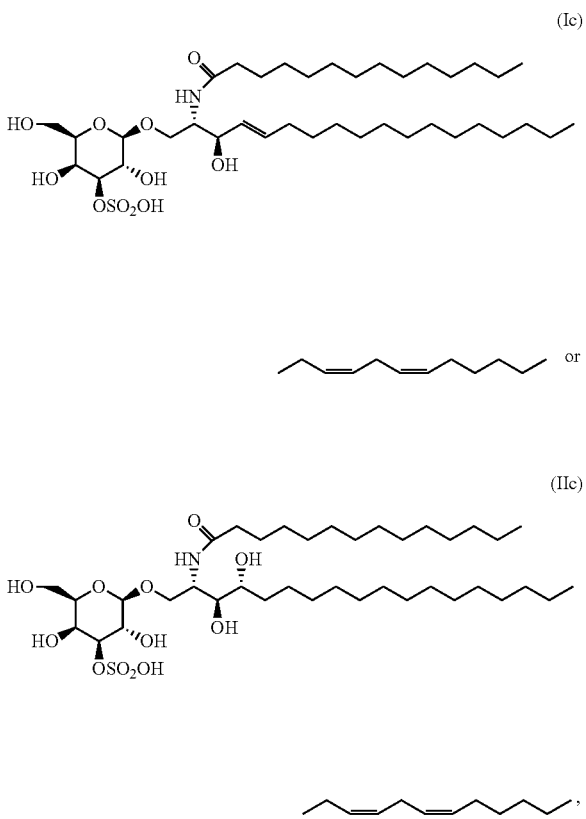

or a pharmaceutically acceptable salt thereof.

2. The compound or salt of claim 1, wherein the compound has the formula (Ic):

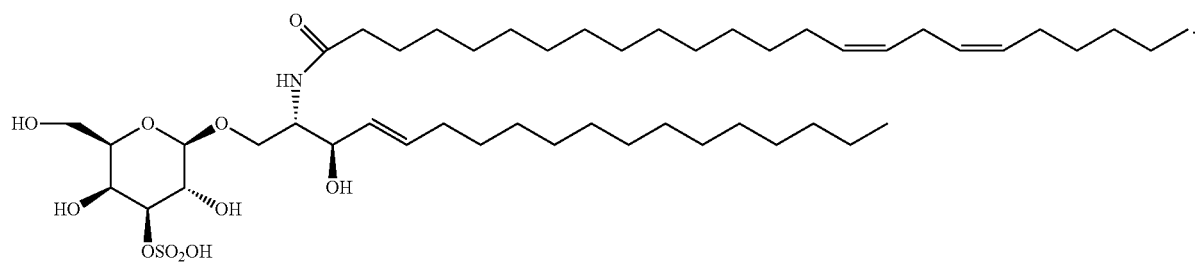
(Ic)
3. The compound or salt of claim 1, wherein the compound has the formula (IIc):
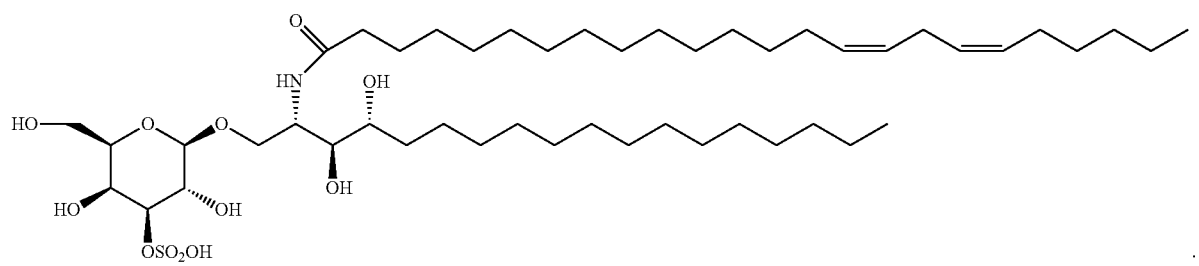
(IIc)
4. A composition comprising a compound or salt of claim 1 and a pharmaceutically acceptable carrier.
5. The composition of claim 4, further comprising a therapeutically effective amount of a compound of
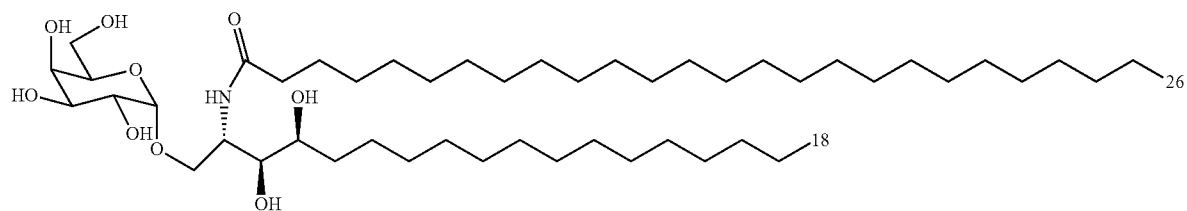
or a salt thereof.
* * * * *